(12) United States Patent
Lu

(10) Patent No.: US 9,078,911 B2
(45) Date of Patent: Jul. 14, 2015

(54) ANTISENSE OLIGONUCLEOTIDES

(75) Inventor: Qi Long Lu, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 501 days.

(21) Appl. No.: 13/369,050

(22) Filed: Feb. 8, 2012

(65) Prior Publication Data

US 2012/0202752 A1 Aug. 9, 2012

Related U.S. Application Data

(60) Provisional application No. 61/440,603, filed on Feb. 8, 2011.

(51) Int. Cl.
| | |
|---|---|
| *C12N 15/11* | (2006.01) |
| *A61K 31/7088* | (2006.01) |
| *A61K 31/7105* | (2006.01) |
| *C12N 15/113* | (2010.01) |

(52) U.S. Cl.
CPC ......... *A61K 31/7088* (2013.01); *A61K 31/7105* (2013.01); *C12N 15/113* (2013.01); *C12N 2310/11* (2013.01); *C12N 2310/315* (2013.01); *C12N 2310/3233* (2013.01); *C12N 2310/346* (2013.01); *C12N 2320/33* (2013.01)

(58) Field of Classification Search
CPC ............. C12N 15/113; C12N 2320/33; A61K 31/7088
See application file for complete search history.

(56) References Cited

U.S. PATENT DOCUMENTS

2010/0130591 A1   5/2010   Sazani et al.

FOREIGN PATENT DOCUMENTS

| CN | 101896186 A | 11/2010 |
|---|---|---|
| EP | 1 160 318 A2 | 12/2001 |
| WO | WO 2006/000057 A1 | 1/2006 |
| WO | WO 2009/054725 A2 | 4/2009 |
| WO | WO 2010/050802 A2 | 5/2010 |
| WO | WO 2010/123369 A1 | 10/2010 |
| WO | WO 2011/057350 A1 | 5/2011 |

OTHER PUBLICATIONS

Invitation to Pay Additional Fees and Partial International Search Report for International Application No. PCT/US2012/024230, mailed Apr. 23, 2012.
Aartsma-Rus, A., et al.; "Antisense-Induced Multiexon Skipping for Duchenne Muscular Dystrophy Makes More Sense"; American Journal of Human Genetics, Chicago, IL; vol. 74; No. 1; Jan. 2004; pp. 83-92.
Aartsma-Rus, A., et al.; "Antisense-mediated modulation of splicing: Therapeutic implications for Duchenne muscular dystrophy"; RNA Biology; vol. 7; No. 4; Jul. 2010; pp. 453-461.
Aartsma-Rus, A., et al.; "Exonic Sequences Provide Better Targets for Antisense Oligonucleotides Than Splice Site Sequences in the Modulation of Duchenne Muscular Dystrophy Splicing"; Oligonucleotides; New York, NY; vol. 20; No. 2; Apr. 2010; pp. 69-77.
Aartsma-Rus, A., et al.; "Functional Analysis of 114 Exon-Internal AONs for Targeted DMD Exon Skipping: Indication for Steric Hindrance of SR Protein Binding Sites"; Oligonucleotides; New York, NY; vol. 15; No. 4; Dec. 2005; pp. 284-297.
Wilton, S.D., et al.; "Antisense Oligonucleotide-Induced Exon Skipping Across the Human Dystrophin Gene Transcript"; Molecular Therapy, Nature Publishing Group; Great Britain; vol. 15; No. 7; Jul. 2007; pp. 1288-1296.

*Primary Examiner* — Jon E Angell
(74) *Attorney, Agent, or Firm* — Alston & Bird LLP

(57) ABSTRACT

Embodiments of the present invention are directed generally to antisense compounds and compositions for the treatment of muscular dystrophy, and in particular, Duchenne muscular dystrophy (DMD). In one embodiment, the invention is directed to antisense oligonucleotide molecules, pharmaceutical compositions and formulations comprising antisense oligonucleotide molecules, and methods of treating muscular dystrophy related diseases and disorders wherein the antisense oligonucleotide molecules comprises a base sequence selected from the group consisting of SEQ ID NO: 5-8, 10, 12, 14, 16, 24, 27, 28, 34, 35, 37, 40, 42, 44-46, 79, 97, 100, 101, and 116, and combinations thereof.

11 Claims, 7 Drawing Sheets

Figure 1:
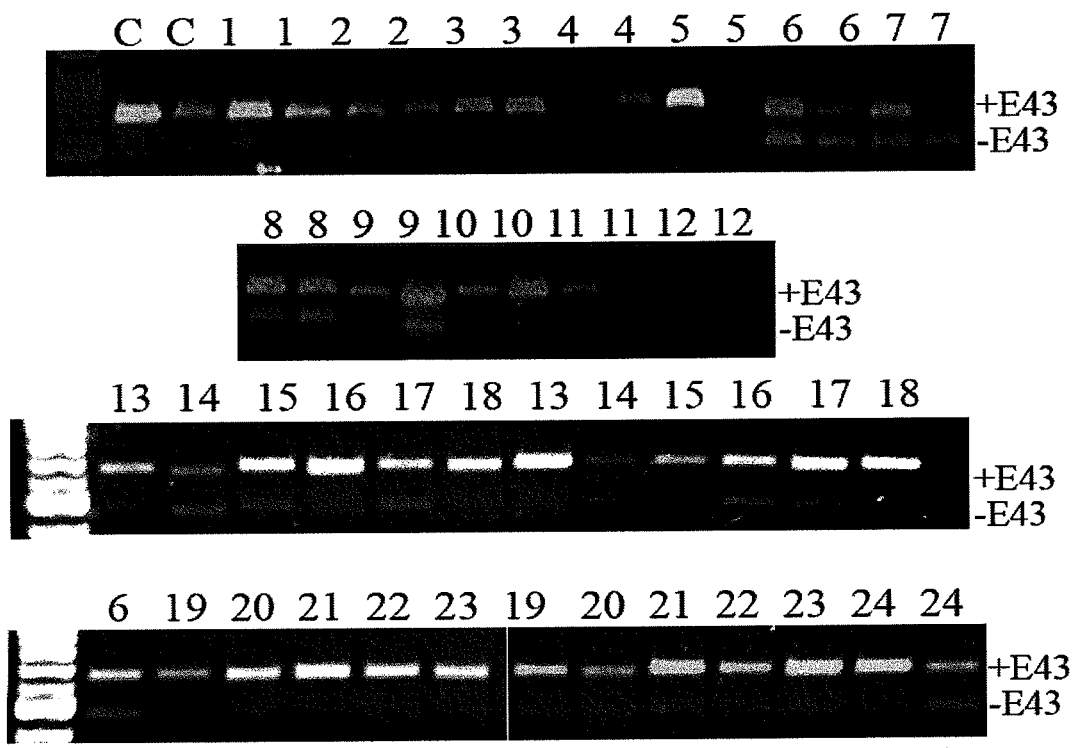

In Vivo exon 43 skipping with 24 AOs in the hDMD mice

In Vivo exon 45 skipping in the hDMD mice

In vivo demonstration of PMOs targeting human dystrophin exon 50 in the hDMD mice Effect of PMO (tagged with vivo-polymer by Genetools) for human dystrophin exon 50 skipping systemically in the hDMD mice.

In Vivo exon 51 skipping in the hDMD mice

In Vivo exon 53 skipping in the hDMD mice

Chemical structure of the polymers used for the delivery of PMO in cell culture and in vivo in the hDMD mice.

SEQUENCE LISTING

<160> NUMBER OF SEQ ID NOS: 118

<210> SEQ ID NO 1
<211> LENGTH: 28
<212> TYPE: DNA
<213> ORGANISM: Artificial Sequence
<220> FEATURE:
<223> OTHER INFORMATION: synthetic HE43 (-1+27)

<400> SEQUENCE: 1
gctttgttgt agactatctt ttatattc                                    28

<210> SEQ ID NO 2
<211> LENGTH: 28
<212> TYPE: DNA
<213> ORGANISM: Artificial Sequence
<220> FEATURE:
<223> OTHER INFORMATION: synthetic HE43 (+9+36)

<400> SEQUENCE: 2
ccgacctgag ctttgttgta gactatct                                    28

<210> SEQ ID NO 3
<211> LENGTH: 28
<212> TYPE: DNA

```
<213> ORGANISM: Artificial Sequence
<220> FEATURE:
<223> OTHER INFORMATION: synthetic HE43(+85+112)

<400> SEQUENCE: 3
cttcctgtag cttcaccctt tccacagg                                            28

<210> SEQ ID NO 4
<211> LENGTH: 28
<212> TYPE: DNA
<213> ORGANISM: Artificial Sequence
<220> FEATURE:
<223> OTHER INFORMATION: synthetic HE43(+97+124)

<400> SEQUENCE: 4
gctgggagag agcttcctgt agcttcac                                            28

<210> SEQ ID NO 5
<211> LENGTH: 28
<212> TYPE: DNA
<213> ORGANISM: Artificial Sequence
<220> FEATURE:
<223> OTHER INFORMATION: synthetic HE43(+156-10)

<400> SEQUENCE: 5
tgttacctac ccttgtcggt ccttgtac                                            28

<210> SEQ ID NO 6
<211> LENGTH: 28
<212> TYPE: DNA
<213> ORGANISM: Artificial Sequence
<220> FEATURE:
<223> OTHER INFORMATION: synthetic HE43(+26+53)

<400> SEQUENCE: 6
ctatgaataa tgtcaatccg acctgagc                                            28

<210> SEQ ID NO 7
<211> LENGTH: 28
<212> TYPE: DNA
<213> ORGANISM: Artificial Sequence
<220> FEATURE:
<223> OTHER INFORMATION: synthetic HE43(+40+67)

<400> SEQUENCE: 7
ctgctgtctt cttgctatga ataatgtc                                            28

<210> SEQ ID NO 8
<211> LENGTH: 28
<212> TYPE: DNA
<213> ORGANISM: Artificial Sequence
<220> FEATURE:
<223> OTHER INFORMATION: synthetic HE43(+59+86)

<400> SEQUENCE: 8
ggcgttgcac tttgcaatgc tgctgtct                                            28

<210> SEQ ID NO 9
<211> LENGTH: 28
<212> TYPE: DNA
<213> ORGANISM: Artificial Sequence
<220> FEATURE:
<223> OTHER INFORMATION: synthetic HE43(+108+135)

<400> SEQUENCE: 9
ttggaaatca agctgggaga gagcttcc                                            28
```

<210> SEQ ID NO 10
<211> LENGTH: 28
<212> TYPE: DNA
<213> ORGANISM: Artificial Sequence
<220> FEATURE:
<223> OTHER INFORMATION: synthetic HE43(+118+145)

<400> SEQUENCE: 10
cttttcccca ttggaaatca agctggga                                28

<210> SEQ ID NO 11
<211> LENGTH: 28
<212> TYPE: DNA
<213> ORGANISM: Artificial Sequence
<220> FEATURE:
<223> OTHER INFORMATION: synthetic HE43(+142+169)

<400> SEQUENCE: 11
gtcggtcctt gtacattttg ttaacttt                                28

<210> SEQ ID NO 12
<211> LENGTH: 28
<212> TYPE: DNA
<213> ORGANISM: Artificial Sequence
<220> FEATURE:
<223> OTHER INFORMATION: synthetic HE43(+150-4)

<400> SEQUENCE: 12
ctacccttgt cggtccttgt acattttg                                28

<210> SEQ ID NO 13
<211> LENGTH: 28
<212> TYPE: DNA
<213> ORGANISM: Artificial Sequence
<220> FEATURE:
<223> OTHER INFORMATION: synthetic HE43(+7+34)

<400> SEQUENCE: 13
gacctgagct tgttgtaga ctatcttt                                 28

<210> SEQ ID NO 14
<211> LENGTH: 28
<212> TYPE: DNA
<213> ORGANISM: Artificial Sequence
<220> FEATURE:
<223> OTHER INFORMATION: synthetic HE43(+14+42)

<400> SEQUENCE: 14
gtcaatccga cctgagcttt gttgtaga                                28

<210> SEQ ID NO 15
<211> LENGTH: 28
<212> TYPE: DNA
<213> ORGANISM: Artificial Sequence
<220> FEATURE:
<223> OTHER INFORMATION: synthetic HE43(+19+46)

<400> SEQUENCE: 15
taatgtcaat ccgacctgag ctttgttg                                28

<210> SEQ ID NO 16
<211> LENGTH: 27
<212> TYPE: DNA
<213> ORGANISM: Artificial Sequence
<220> FEATURE:

<223> OTHER INFORMATION: synthetic HE43(+31+57)

<400> SEQUENCE: 16
cttgctatga ataatgtcaa tccgacc                                    27

<210> SEQ ID NO 17
<211> LENGTH: 28
<212> TYPE: DNA
<213> ORGANISM: Artificial Sequence
<220> FEATURE:
<223> OTHER INFORMATION: synthetic HE43(+35+62)

<400> SEQUENCE: 17
gtcttcttgc tatgaataat gtcaatcc                                   28

<210> SEQ ID NO 18
<211> LENGTH: 28
<212> TYPE: DNA
<213> ORGANISM: Artificial Sequence
<220> FEATURE:
<223> OTHER INFORMATION: synthetic HE43(+53+80)

<400> SEQUENCE: 18
gcactttgca atgctgctgt cttcttgc                                   28

<210> SEQ ID NO 19
<211> LENGTH: 28
<212> TYPE: DNA
<213> ORGANISM: Artificial Sequence
<220> FEATURE:
<223> OTHER INFORMATION: synthetic HE43(+64+91)

<400> SEQUENCE: 19
ccacaggcgt tgcactttgc aatgctgc                                   28

<210> SEQ ID NO 20
<211> LENGTH: 28
<212> TYPE: DNA
<213> ORGANISM: Artificial Sequence
<220> FEATURE:
<223> OTHER INFORMATION: synthetic HE43(+77+104)

<400> SEQUENCE: 20
agcttcaccc tttccacagg cgttgcac                                   28

<210> SEQ ID NO 21
<211> LENGTH: 23
<212> TYPE: DNA
<213> ORGANISM: Artificial Sequence
<220> FEATURE:
<223> OTHER INFORMATION: synthetic HE43(+78+100)

<400> SEQUENCE: 21 tcacccttc cacaggcgtt gca                                         23

<210> SEQ ID NO 22
<211> LENGTH: 20
<212> TYPE: DNA
<213> ORGANISM: Artificial Sequence
<220> FEATURE:
<223> OTHER INFORMATION: synthetic HE43(+101+120)

<400> SEQUENCE: 22
ggagagagct tcctgtagct                                            20

```
<210> SEQ ID NO 23
<211> LENGTH: 28
<212> TYPE: DNA
<213> ORGANISM: Artificial Sequence
<220> FEATURE:
<223> OTHER INFORMATION: synthetic HE43(+113+140)

<400> SEQUENCE: 23
tcccattgga aatcaagctg ggagagag                                    28

<210> SEQ ID NO 24
<211> LENGTH: 28
<212> TYPE: DNA
<213> ORGANISM: Artificial Sequence
<220> FEATURE:
<223> OTHER INFORMATION: synthetic HE43(+162-16)

<400> SEQUENCE: 24
tatatgtgtt acctaccctt gtcggtcc                                    28

<210> SEQ ID NO 25
<211> LENGTH: 27
<212> TYPE: DNA
<213> ORGANISM: Artificial Sequence
<220> FEATURE:
<223> OTHER INFORMATION: synthetic HE45 (-12+15)

<400> SEQUENCE: 25
gccatcctgg agttcctgta agatacc                                     27

<210> SEQ ID NO 26
<211> LENGTH: 25
<212> TYPE: DNA
<213> ORGANISM: Artificial Sequence
<220> FEATURE:
<223> OTHER INFORMATION: synthetic HE45 (-19+6)

<400> SEQUENCE: 26
gagttcctgt aagataccaa aaagg                                       25

<210> SEQ ID NO 27
<211> LENGTH: 25
<212> TYPE: DNA
<213> ORGANISM: Artificial Sequence
<220> FEATURE:
<223> OTHER INFORMATION: synthetic HE45(-3+22)

<400> SEQUENCE: 27
gcccaatgcc atcctggagt tcctg                                       25

<210> SEQ ID NO 28
<211> LENGTH: 22
<212> TYPE: DNA
<213> ORGANISM: Artificial Sequence
<220> FEATURE:
<223> OTHER INFORMATION: synthetic HE45(-2+20)

<400> SEQUENCE: 28
ccaatgccat cctggagttc ct                                          22

<210> SEQ ID NO 29
<211> LENGTH: 24
<212> TYPE: DNA
<213> ORGANISM: Artificial Sequence
<220> FEATURE:
<223> OTHER INFORMATION: synthetic HE45(-6+18)
```

-continued

<400> SEQUENCE: 29
aatgccatcc tggagttcct gtaa                                      24

<210> SEQ ID NO 30
<211> LENGTH: 25
<212> TYPE: DNA
<213> ORGANISM: Artificial Sequence
<220> FEATURE:
<223> OTHER INFORMATION: synthetic HE45(-15+10)

<400> SEQUENCE: 30
cctggagttc ctgtaagata ccaaa                                     25

<210> SEQ ID NO 31
<211> LENGTH: 25
<212> TYPE: DNA
<213> ORGANISM: Artificial Sequence
<220> FEATURE:
<223> OTHER INFORMATION: synthetic HE45(-9+16)

<400> SEQUENCE: 31
tgccatcctg gagttcctgt aagat                                     25

<210> SEQ ID NO 32
<211> LENGTH: 22
<212> TYPE: DNA
<213> ORGANISM: Artificial Sequence
<220> FEATURE:
<223> OTHER INFORMATION: synthetic HE45(-11+11)

<400> SEQUENCE: 32
tcctggagtt cctgtaagat ac                                        22

<210> SEQ ID NO 33
<211> LENGTH: 25
<212> TYPE: DNA
<213> ORGANISM: Artificial Sequence
<220> FEATURE:
<223> OTHER INFORMATION: synthetic HE45(-11+14)

<400> SEQUENCE: 33
ccatcctgga gttcctgtaa gatac                                     25

<210> SEQ ID NO 34
<211> LENGTH: 29
<212> TYPE: DNA
<213> ORGANISM: Artificial Sequence
<220> FEATURE:
<223> OTHER INFORMATION: synthetic HE45(-8+21)

<400> SEQUENCE: 34
cccaatgcca tcctggagtt cctgtaaga                                 29

<210> SEQ ID NO 35
<211> LENGTH: 28
<212> TYPE: DNA
<213> ORGANISM: Artificial Sequence
<220> FEATURE:
<223> OTHER INFORMATION: synthetic HE45(-1+27)

<400> SEQUENCE: 35
ccgctgccca atgccatcct ggagttcc                                  28

<210> SEQ ID NO 36
<211> LENGTH: 30

```
<212> TYPE: DNA
<213> ORGANISM: Artificial Sequence
<220> FEATURE:
<223> OTHER INFORMATION: synthetic HE45(-11+19)

<400> SEQUENCE: 36
caatgccatc ctggagttcc tgtaagatac                                30

<210> SEQ ID NO 37
<211> LENGTH: 30
<212> TYPE: DNA
<213> ORGANISM: Artificial Sequence
<220> FEATURE:
<223> OTHER INFORMATION: synthetic HE45(-9+21)

<400> SEQUENCE: 37
cccaatgcca tcctggagtt cctgtaagat                                30

<210> SEQ ID NO 38
<211> LENGTH: 30
<212> TYPE: DNA
<213> ORGANISM: Artificial Sequence
<220> FEATURE:
<223> OTHER INFORMATION: synthetic HE45(-2+28)

<400> SEQUENCE: 38
gccgctgccc aatgccatcc tggagttcct                                30

<210> SEQ ID NO 39
<211> LENGTH: 30
<212> TYPE: DNA
<213> ORGANISM: Artificial Sequence
<220> FEATURE:
<223> OTHER INFORMATION: synthetic HE45(-12+18)

<400> SEQUENCE: 39
aatgccatcc tggagttcct gtaagatacc                                30

<210> SEQ ID NO 40
<211> LENGTH: 30
<212> TYPE: DNA
<213> ORGANISM: Artificial Sequence
<220> FEATURE:
<223> OTHER INFORMATION: synthetic HE45(-3+27)

<400> SEQUENCE: 40
ccgctgccca atgccatcct ggagttcctg                                30

<210> SEQ ID NO 41
<211> LENGTH: 30
<212> TYPE: DNA
<213> ORGANISM: Artificial Sequence
<220> FEATURE:
<223> OTHER INFORMATION: synthetic HE45(-1+29)

<400> SEQUENCE: 41
tgccgctgcc caatgccatc ctggagttcc                                30

<210> SEQ ID NO 42
<211> LENGTH: 30
<212> TYPE: DNA
<213> ORGANISM: Artificial Sequence
<220> FEATURE:
<223> OTHER INFORMATION: synthetic HE45(-7+23)

<400> SEQUENCE: 42
```

```
tgcccaatgc catcctggag ttcctgtaag                                    30
```

<210> SEQ ID NO 43
<211> LENGTH: 28
<212> TYPE: DNA
<213> ORGANISM: Artificial Sequence
<220> FEATURE:
<223> OTHER INFORMATION: synthetic HE45(-9+19)

<400> SEQUENCE: 43

```
caatgccatc ctggagttcc tgtaagat                                      28
```

<210> SEQ ID NO 44
<211> LENGTH: 28
<212> TYPE: DNA
<213> ORGANISM: Artificial Sequence
<220> FEATURE:
<223> OTHER INFORMATION: synthetic HE45(-7+21)

<400> SEQUENCE: 44

```
cccaatgcca tcctggagtt cctgtaag                                      28
```

<210> SEQ ID NO 45
<211> LENGTH: 28
<212> TYPE: DNA
<213> ORGANISM: Artificial Sequence
<220> FEATURE:
<223> OTHER INFORMATION: synthetic HE45(-5+23)

<400> SEQUENCE: 45

```
tgcccaatgc catcctggag ttcctgta                                      28
```

<210> SEQ ID NO 46
<211> LENGTH: 28
<212> TYPE: DNA
<213> ORGANISM: Artificial Sequence
<220> FEATURE:
<223> OTHER INFORMATION: synthetic HE45(-3+25)

<400> SEQUENCE: 46

```
gctgcccaat gccatcctgg agttcctg                                      28
```

<210> SEQ ID NO 47
<211> LENGTH: 25
<212> TYPE: DNA
<213> ORGANISM: Artificial Sequence
<220> FEATURE:
<223> OTHER INFORMATION: synthetic HE45(-12+13)

<400> SEQUENCE: 47

```
catcctggag ttcctgtaag atacc                                         25
```

<210> SEQ ID NO 48
<211> LENGTH: 27
<212> TYPE: DNA
<213> ORGANISM: Artificial Sequence
<220> FEATURE:
<223> OTHER INFORMATION: synthetic HE45(-12+15)

<400> SEQUENCE: 48

```
gccatcctgg agttcctgta agatacc                                       27
```

<210> SEQ ID NO 49
<211> LENGTH: 25
<212> TYPE: DNA
<213> ORGANISM: Artificial Sequence

```
<220> FEATURE:
<223> OTHER INFORMATION: synthetic E45+1+25

<400> SEQUENCE: 49
gctgcccaat gccatcctgg agttc                                         25

<210> SEQ ID NO 50
<211> LENGTH: 20
<212> TYPE: DNA
<213> ORGANISM: Artificial Sequence
<220> FEATURE:
<223> OTHER INFORMATION: synthetic E45+3+22

<400> SEQUENCE: 50
gcccaatgcc atcctggagt                                               20

<210> SEQ ID NO 51
<211> LENGTH: 25
<212> TYPE: DNA
<213> ORGANISM: Artificial Sequence
<220> FEATURE:
<223> OTHER INFORMATION: synthetic E45+5+29

<400> SEQUENCE: 51
tgccgctgcc caatgccatc ctgga                                         25

<210> SEQ ID NO 52
<211> LENGTH: 19
<212> TYPE: DNA
<213> ORGANISM: Artificial Sequence
<220> FEATURE:
<223> OTHER INFORMATION: synthetic E45+6+24

<400> SEQUENCE: 52
ctgcccaatg ccatcctgg                                                19

<210> SEQ ID NO 53
<211> LENGTH: 26
<212> TYPE: DNA
<213> ORGANISM: Artificial Sequence
<220> FEATURE:
<223> OTHER INFORMATION: synthetic E45+9+34

<400> SEQUENCE: 53
cagtttgccg ctgcccaatg ccatcc                                        26

<210> SEQ ID NO 54
<211> LENGTH: 24
<212> TYPE: DNA
<213> ORGANISM: Artificial Sequence
<220> FEATURE:
<223> OTHER INFORMATION: synthetic E45+12+35

<400> SEQUENCE: 54
acagtttgcc gctgcccaat gcca                                          24

<210> SEQ ID NO 55
<211> LENGTH: 25
<212> TYPE: DNA
<213> ORGANISM: Artificial Sequence
<220> FEATURE:
<223> OTHER INFORMATION: synthetic E45+17+41

<400> SEQUENCE: 55
ctgacaacag tttgccgctg cccaa                                         25
```

<210> SEQ ID NO 56
<211> LENGTH: 20
<212> TYPE: DNA
<213> ORGANISM: Artificial Sequence
<220> FEATURE:
<223> OTHER INFORMATION: synthetic E45+34+53

<400> SEQUENCE: 56
gcattcaatg ttctgacaac                                            20

<210> SEQ ID NO 57
<211> LENGTH: 30
<212> TYPE: DNA
<213> ORGANISM: Artificial Sequence
<220> FEATURE:
<223> OTHER INFORMATION: synthetic E45+44+73

<400> SEQUENCE: 57
gaattatttc ttccccagtt gcattcaatg                                 30

<210> SEQ ID NO 58
<211> LENGTH: 30
<212> TYPE: DNA
<213> ORGANISM: Artificial Sequence
<220> FEATURE:
<223> OTHER INFORMATION: synthetic E45+69+98

<400> SEQUENCE: 58
ctggcatctg tttttgagga ttgctgaatt                                 30

<210> SEQ ID NO 59
<211> LENGTH: 26
<212> TYPE: DNA
<213> ORGANISM: Artificial Sequence
<220> FEATURE:
<223> OTHER INFORMATION: synthetic E45+34+59

<400> SEQUENCE: 59
ccagttgcat tcaatgttct gacaac                                     26

<210> SEQ ID NO 60
<211> LENGTH: 23
<212> TYPE: DNA
<213> ORGANISM: Artificial Sequence
<220> FEATURE:
<223> OTHER INFORMATION: synthetic E45+56+78

<400> SEQUENCE: 60
ttgctgaatt atttcttccc cag                                        23

<210> SEQ ID NO 61
<211> LENGTH: 29
<212> TYPE: DNA
<213> ORGANISM: Artificial Sequence
<220> FEATURE:
<223> OTHER INFORMATION: synthetic E45+60+88

<400> SEQUENCE: 61
tttttgagga ttgctgaatt atttcttcc                                  29

<210> SEQ ID NO 62
<211> LENGTH: 25
<212> TYPE: DNA
<213> ORGANISM: Artificial Sequence
<220> FEATURE:
<223> OTHER INFORMATION: synthetic E45+88+112

```
<400> SEQUENCE: 62
tttcctgtag aatactggca tctgt                                      25

<210> SEQ ID NO 63
<211> LENGTH: 31
<212> TYPE: DNA
<213> ORGANISM: Artificial Sequence
<220> FEATURE:
<223> OTHER INFORMATION: synthetic E45+92+122

<400> SEQUENCE: 63
cttcccaatt tttcctgtag aatactggca t                               31

<210> SEQ ID NO 64
<211> LENGTH: 25
<212> TYPE: DNA
<213> ORGANISM: Artificial Sequence
<220> FEATURE:
<223> OTHER INFORMATION: synthetic E45+94+118

<400> SEQUENCE: 64 ccaattttc ctgtagaata ctggc                                       25

<210> SEQ ID NO 65
<211> LENGTH: 29
<212> TYPE: DNA
<213> ORGANISM: Artificial Sequence
<220> FEATURE:
<223> OTHER INFORMATION: synthetic E45+98+126

<400> SEQUENCE: 65
caggcttccc aatttttcct gtagaatac                                  29

<210> SEQ ID NO 66
<211> LENGTH: 26
<212> TYPE: DNA
<213> ORGANISM: Artificial Sequence
<220> FEATURE:
<223> OTHER INFORMATION: synthetic E45+119+144

<400> SEQUENCE: 66
ctcctgccac cgcagattca ggcttc                                     26

<210> SEQ ID NO 67
<211> LENGTH: 25
<212> TYPE: DNA
<213> ORGANISM: Artificial Sequence
<220> FEATURE:
<223> OTHER INFORMATION: synthetic E45+126+150

<400> SEQUENCE: 67
gcagacctcc tgccaccgca gattc                                      25

<210> SEQ ID NO 68
<211> LENGTH: 31
<212> TYPE: DNA
<213> ORGANISM: Artificial Sequence
<220> FEATURE:
<223> OTHER INFORMATION: synthetic E45+126+155

<400> SEQUENCE: 68
ttgtttgcag acctcctgcc accgcagatt c                               31

<210> SEQ ID NO 69
```

```
<211> LENGTH: 24
<212> TYPE: DNA
<213> ORGANISM: Artificial Sequence
<220> FEATURE:
<223> OTHER INFORMATION: synthetic E45+134+157

<400> SEQUENCE: 69
gctgtttgca gacctcctgc cacc                                            24

<210> SEQ ID NO 70
<211> LENGTH: 25
<212> TYPE: DNA
<213> ORGANISM: Artificial Sequence
<220> FEATURE:
<223> OTHER INFORMATION: synthetic E45+130+154

<400> SEQUENCE: 70
gtttgcagac ctcctgccac cgcag                                           25

<210> SEQ ID NO 71
<211> LENGTH: 30
<212> TYPE: DNA
<213> ORGANISM: Artificial Sequence
<220> FEATURE:
<223> OTHER INFORMATION: synthetic E45+145+174

<400> SEQUENCE: 71
cttttttctg tctgacagct gtttgcagac                                      30

<210> SEQ ID NO 72
<211> LENGTH: 21
<212> TYPE: DNA
<213> ORGANISM: Artificial Sequence
<220> FEATURE:
<223> OTHER INFORMATION: synthetic E45+147+167

<400> SEQUENCE: 72
ctgtctgaca gctgtttgca g                                               21

<210> SEQ ID NO 73
<211> LENGTH: 25
<212> TYPE: DNA
<213> ORGANISM: Artificial Sequence
<220> FEATURE:
<223> OTHER INFORMATION: synthetic E45+156-4

<400> SEQUENCE: 73
ctacctcttt tttctgtctg acagc                                           25

<210> SEQ ID NO 74
<211> LENGTH: 25
<212> TYPE: DNA
<213> ORGANISM: Artificial Sequence
<220> FEATURE:
<223> OTHER INFORMATION: synthetic E45+170-20

<400> SEQUENCE: 74
tattagatct gtcgccctac ctctt                                           25

<210> SEQ ID NO 75
<211> LENGTH: 25
<212> TYPE: DNA
<213> ORGANISM: Artificial Sequence
<220> FEATURE:
<223> OTHER INFORMATION: synthetic E45+174-22

<400> SEQUENCE: 75
```

```
cctattagat ctgtcgccct acctc                                              25
```

<210> SEQ ID NO 76
<211> LENGTH: 19
<212> TYPE: RNA
<213> ORGANISM: Artificial Sequence
<220> FEATURE:
<223> OTHER INFORMATION: synthetic HE50 (-19-1)

<400> SEQUENCE: 76

```
cuuuaacaga aaagcauac                                                     19
```

<210> SEQ ID NO 77
<211> LENGTH: 20
<212> TYPE: RNA
<213> ORGANISM: Artificial Sequence
<220> FEATURE:
<223> OTHER INFORMATION: synthetic HE50 (-19+1)

<400> SEQUENCE: 77

```
ucuuuaacag aaaagcauac                                                    20
```

<210> SEQ ID NO 78
<211> LENGTH: 22
<212> TYPE: RNA
<213> ORGANISM: Artificial Sequence
<220> FEATURE:
<223> OTHER INFORMATION: synthetic HE50(-19+3)

<400> SEQUENCE: 78

```
ccucuuuaac agaaaagcau ac                                                 22
```

<210> SEQ ID NO 79
<211> LENGTH: 27
<212> TYPE: RNA
<213> ORGANISM: Artificial Sequence
<220> FEATURE:
<223> OTHER INFORMATION: synthetic HE50(-19+8)

<400> SEQUENCE: 79

```
aacuuccucu uuaacagaaa agcauac                                            27
```

<210> SEQ ID NO 80
<211> LENGTH: 32
<212> TYPE: RNA
<213> ORGANISM: Artificial Sequence
<220> FEATURE:
<223> OTHER INFORMATION: synthetic HE50(-19+13)

<400> SEQUENCE: 80

```
cuucuaacuu ccucuuuaac agaaaagcau ac                                      32
```

<210> SEQ ID NO 81
<211> LENGTH: 16
<212> TYPE: RNA
<213> ORGANISM: Artificial Sequence
<220> FEATURE:
<223> OTHER INFORMATION: synthetic HE50(-13+3)

<400> SEQUENCE: 81

```
ccucuuuaac agaaaa                                                        16
```

<210> SEQ ID NO 82
<211> LENGTH: 22
<212> TYPE: RNA

```
<213> ORGANISM: Artificial Sequence
<220> FEATURE:
<223> OTHER INFORMATION: synthetic HE50(-14+8)

<400> SEQUENCE: 82
aacuuccucu uuaacagaaa ag                                              22

<210> SEQ ID NO 83
<211> LENGTH: 17
<212> TYPE: RNA
<213> ORGANISM: Artificial Sequence
<220> FEATURE:
<223> OTHER INFORMATION: synthetic HE50(-9+8)

<400> SEQUENCE: 83
aacuuccucu uuaacag                                                    17

<210> SEQ ID NO 84
<211> LENGTH: 30
<212> TYPE: RNA
<213> ORGANISM: Artificial Sequence
<220> FEATURE:
<223> OTHER INFORMATION: synthetic HE50(-9+21)

<400> SEQUENCE: 84
gcucagaucu ucuaacuucc ucuuuaacag                                      30

<210> SEQ ID NO 85
<211> LENGTH: 16
<212> TYPE: RNA
<213> ORGANISM: Artificial Sequence
<220> FEATURE:
<223> OTHER INFORMATION: synthetic HE50(-8+8)

<400> SEQUENCE: 85
aacuuccucu uuaaca                                                     16

<210> SEQ ID NO 86
<211> LENGTH: 29
<212> TYPE: RNA
<213> ORGANISM: Artificial Sequence
<220> FEATURE:
<223> OTHER INFORMATION: synthetic HE50(+2+30)

<400> SEQUENCE: 86
ccacucagag cucagaucuu cuaacuucc                                       29

<210> SEQ ID NO 87
<211> LENGTH: 17
<212> TYPE: RNA
<213> ORGANISM: Artificial Sequence
<220> FEATURE:
<223> OTHER INFORMATION: synthetic HE50(+11+27)

<400> SEQUENCE: 87
cucagagcuc agaucuu                                                    17

<210> SEQ ID NO 88
<211> LENGTH: 17
<212> TYPE: RNA
<213> ORGANISM: Artificial Sequence
<220> FEATURE:
<223> OTHER INFORMATION: synthetic HE50(+42+58)

<400> SEQUENCE: 88
gcucuugaag uaaacgg                                                    17
```

<210> SEQ ID NO 89
<211> LENGTH: 18
<212> TYPE: RNA
<213> ORGANISM: Artificial Sequence
<220> FEATURE:
<223> OTHER INFORMATION: synthetic HE50(+85+102)

<400> SEQUENCE: 89
aauagugguc aguccagg                                                   18

<210> SEQ ID NO 90
<211> LENGTH: 23
<212> TYPE: RNA
<213> ORGANISM: Artificial Sequence
<220> FEATURE:
<223> OTHER INFORMATION: synthetic HE50(+92-5)

<400> SEQUENCE: 90
cuuacaggcu ccaauagugg uca                                             23

<210> SEQ ID NO 91
<211> LENGTH: 28
<212> TYPE: RNA
<213> ORGANISM: Artificial Sequence
<220> FEATURE:
<223> OTHER INFORMATION: synthetic HE50(+92-10)

<400> SEQUENCE: 91
guauacuuac aggcuccaau agugguca                                        28

<210> SEQ ID NO 92
<211> LENGTH: 30
<212> TYPE: RNA
<213> ORGANISM: Artificial Sequence
<220> FEATURE:
<223> OTHER INFORMATION: synthetic HE50(+94-14)

<400> SEQUENCE: 92
uccaguauac uuacaggcuc caauagggu                                       30

<210> SEQ ID NO 93
<211> LENGTH: 18
<212> TYPE: RNA
<213> ORGANISM: Artificial Sequence
<220> FEATURE:
<223> OTHER INFORMATION: synthetic HE50(+97-5)

<400> SEQUENCE: 93
cuuacaggcu ccaauagu                                                   18

<210> SEQ ID NO 94
<211> LENGTH: 23
<212> TYPE: RNA
<213> ORGANISM: Artificial Sequence
<220> FEATURE:
<223> OTHER INFORMATION: synthetic HE50(+97-10)

<400> SEQUENCE: 94
guauacuuac aggcuccaau agu                                             23

<210> SEQ ID NO 95
<211> LENGTH: 27
<212> TYPE: RNA
<213> ORGANISM: Artificial Sequence
<220> FEATURE:

```
<223> OTHER INFORMATION: synthetic HE50(+97-14)

<400> SEQUENCE: 95
uccaguauac uuacaggcuc caauagu                                    27

<210> SEQ ID NO 96
<211> LENGTH: 22
<212> TYPE: RNA
<213> ORGANISM: Artificial Sequence
<220> FEATURE:
<223> OTHER INFORMATION: synthetic HE50(+102-14)

<400> SEQUENCE: 96
uccaguauac uuacaggcuc ca                                         22

<210> SEQ ID NO 97
<211> LENGTH: 25
<212> TYPE: RNA
<213> ORGANISM: Artificial Sequence
<220> FEATURE:
<223> OTHER INFORMATION: synthetic HE50(+103-18)

<400> SEQUENCE: 97
gggauccagu auacuuacag gcucc                                      25

<210> SEQ ID NO 98
<211> LENGTH: 19
<212> TYPE: RNA
<213> ORGANISM: Artificial Sequence
<220> FEATURE:
<223> OTHER INFORMATION: synthetic HE50(+105-14)

<400> SEQUENCE: 98
uccaguauac uuacaggcu                                             19

<210> SEQ ID NO 99
<211> LENGTH: 15
<212> TYPE: RNA
<213> ORGANISM: Artificial Sequence
<220> FEATURE:
<223> OTHER INFORMATION: synthetic HE50(+109-14)

<400> SEQUENCE: 99
uccaguauac uuaca                                                 15

<210> SEQ ID NO 100
<211> LENGTH: 28
<212> TYPE: DNA
<213> ORGANISM: Artificial Sequence
<220> FEATURE:
<223> OTHER INFORMATION: synthetic HE51 (+68+95)

<400> SEQUENCE: 100
ctccaacatc aaggaagatg gcatttct                                   28

<210> SEQ ID NO 101
<211> LENGTH: 25
<212> TYPE: DNA
<213> ORGANISM: Artificial Sequence
<220> FEATURE:
<223> OTHER INFORMATION: synthetic HE51 (+65+89)

<400> SEQUENCE: 101
catcaaggaa gatggcattt ctagt                                      25
```

<210> SEQ ID NO 102
<211> LENGTH: 26
<212> TYPE: DNA
<213> ORGANISM: Artificial Sequence
<220> FEATURE:
<223> OTHER INFORMATION: synthetic HE51 (-22+4)

<400> SEQUENCE: 102
ggagctaaaa tattttgggt ttttgc                                          26

<210> SEQ ID NO 103
<211> LENGTH: 25
<212> TYPE: DNA
<213> ORGANISM: Artificial Sequence
<220> FEATURE:
<223> OTHER INFORMATION: synthetic HE51 (+220-11)

<400> SEQUENCE: 103
ttttctcata ccttctgctt gatga                                           25

<210> SEQ ID NO 104
<211> LENGTH: 27
<212> TYPE: DNA
<213> ORGANISM: Artificial Sequence
<220> FEATURE:
<223> OTHER INFORMATION: synthetic HE51 (+74+101)

<400> SEQUENCE: 104
aggtacctcc aacatcaagg aagatgg                                         27

<210> SEQ ID NO 105
<211> LENGTH: 25
<212> TYPE: DNA
<213> ORGANISM: Artificial Sequence
<220> FEATURE:
<223> OTHER INFORMATION: synthetic HE51(+71+95)

<400> SEQUENCE: 105
ctccaacatc aaggaagatg gcatt                                           25

<210> SEQ ID NO 106
<211> LENGTH: 28
<212> TYPE: DNA
<213> ORGANISM: Artificial Sequence
<220> FEATURE:
<223> OTHER INFORMATION: synthetic HE51(+68+95)

<400> SEQUENCE: 106
ctccaacatc aaggaagatg gcatttct                                        28

<210> SEQ ID NO 107
<211> LENGTH: 30
<212> TYPE: DNA
<213> ORGANISM: Artificial Sequence
<220> FEATURE:
<223> OTHER INFORMATION: synthetic HE51(+66+95)

<400> SEQUENCE: 107
ctccaacatc aaggaagatg gcatttctag                                      30

<210> SEQ ID NO 108
<211> LENGTH: 25
<212> TYPE: DNA
<213> ORGANISM: Artificial Sequence
<220> FEATURE:
<223> OTHER INFORMATION: synthetic HE51(+61+85)

```
<400> SEQUENCE: 108
aaggaagatg gcatttctag tttgg                                          25

<210> SEQ ID NO 109
<211> LENGTH: 25
<212> TYPE: DNA
<213> ORGANISM: Artificial Sequence
<220> FEATURE:
<223> OTHER INFORMATION: synthetic HE51(-10+15)

<400> SEQUENCE: 109
cagtctgagt aggagctaaa atatt                                          25

<210> SEQ ID NO 110
<211> LENGTH: 25
<212> TYPE: DNA
<213> ORGANISM: Artificial Sequence
<220> FEATURE:
<223> OTHER INFORMATION: synthetic HE51(-16+9)

<400> SEQUENCE: 110
gagtaggagc taaaatattt tgggt                                          25

<210> SEQ ID NO 111
<211> LENGTH: 25
<212> TYPE: RNA
<213> ORGANISM: Artificial Sequence
<220> FEATURE:
<223> OTHER INFORMATION: synthetic HE53 (-11+14)

<400> SEQUENCE: 111
cugaauucuu ucaacuagaa uaaaa                                          25

<210> SEQ ID NO 112
<211> LENGTH: 28
<212> TYPE: RNA
<213> ORGANISM: Artificial Sequence
<220> FEATURE:
<223> OTHER INFORMATION: synthetic HE53 (+69+96)

<400> SEQUENCE: 112 gccaugugu ugaauccuuu aacauuuc                                        28

<210> SEQ ID NO 113
<211> LENGTH: 25
<212> TYPE: RNA
<213> ORGANISM: Artificial Sequence
<220> FEATURE:
<223> OTHER INFORMATION: synthetic HE53(+134+158)

<400> SEQUENCE: 113
ccaugacuca agcuuggcuc uggcc                                          25

<210> SEQ ID NO 114
<211> LENGTH: 20
<212> TYPE: RNA
<213> ORGANISM: Artificial Sequence
<220> FEATURE:
<223> OTHER INFORMATION: synthetic HE53(+168+187)

<400> SEQUENCE: 114
cccuauacag uagaugcaau                                                20

<210> SEQ ID NO 115
<211> LENGTH: 24
```

```
<212> TYPE: RNA
<213> ORGANISM: Artificial Sequence
<220> FEATURE:
<223> OTHER INFORMATION: synthetic HE53(+200-11)

<400> SEQUENCE: 115
uugauacuaa ccuugguuuc ugug                                        24

<210> SEQ ID NO 116
<211> LENGTH: 24
<212> TYPE: DNA
<213> ORGANISM: Artificial Sequence
<220> FEATURE:
<223> OTHER INFORMATION: synthetic HE53 (+42+65)

<400> SEQUENCE: 116
caactgttgc ctccggttct gaag                                        24

<210> SEQ ID NO 117
<211> LENGTH: 24
<212> TYPE: DNA
<213> ORGANISM: Artificial Sequence
<220> FEATURE:
<223> OTHER INFORMATION: synthetic HE53 (+146+169)

<400> SEQUENCE: 117
ggaccctcct tccatgactc aagc                                        24

<210> SEQ ID NO 118
<211> LENGTH: 27
<212> TYPE: DNA
<213> ORGANISM: Artificial Sequence
<220> FEATURE:
<223> OTHER INFORMATION: synthetic HE53 (+204-18)

<400> SEQUENCE: 118
ggtatctttg atactaacct tggtttc                                     27
```

ANTISENSE OLIGONUCLEOTIDES

CROSS REFERENCE TO RELATED APPLICATIONS

This application is related to commonly owned copending Provisional Application Ser. No. 61/440,603, filed Feb. 8, 2011, incorporated herein by reference in its entirety, and claims the benefit of its earlier filing date under 35 U.S.C. 119(e).

FEDERALLY SPONSORED RESEARCH OR DEVELOPMENT

This invention was made with United States Government support under grant No. U01NS062709 awarded by the National Institute of Neurological Disorders and Stroke of the National Institutes of Health (NIH/NINDS) and under grant No. 1P50AR060836-01 awarded by the National Institute of Arthritis and Musculoskeletal and Skin Diseases of the National Institutes of Health (NIH/NIMAS). The United States Government has certain rights in the invention.

BACKGROUND OF THE INVENTION

Duchenne muscular dystrophy (DMD) is the most common and severe form of muscular dystrophy. DMD, which affects 1 of 3500 new-born boys, is a severe x-linked muscle wasting disease caused by nonsense and out of frame mutations of the human DMD gene. DMD patients typically require a wheelchair by age 10 to 12 and die in their late teens to early thirties.

DMD is caused by mutations in the dystrophin gene that preclude the synthesis of functional protein. The dystrophin gene is one of the largest genes in the human genome containing 79 exons spanning more than 2.3 million base pairs. Generally, a mutation in any of the exon portions of the dystrohin gene that result in changes in the reading frame by removal of an entire exon or exons or duplications of one or more exons, or introduces a stop codon, have the potential to disrupt production of functional dystrophin, which may result in DMD.

In recent years, research has shown that therapies based on antisense oligonucleotides (AOs) may provide a promising treatment of genetic related diseases including DMD. In particular, antisense oligonucleotides (AOs) have been developed that exhibit specificity to targeted gene expression. For instance, antisense oligonucleotides have been shown to induce specific exon skipping and thereby restore the reading frame and expression of functional dystrophin. By skipping out-of-frame mutations of the dystrophin gene, the reading frame can be restored and a truncated, yet functional, Becker-like dystrophin protein is expressed.

Studies in human cells in vitro and in animal models of the disease in vivo have proven the principle of exon skipping as a potential therapy for DMD. Initial clinical trials using two different AO chemistries (phosphorodiamidate morpholino oligomer (PMO) and phosphorothioate-linked 2'-.beta.-methyl RNA (2'OMePS)) have recently been performed, with encouraging results. Restoration of dystrophin expression in the TA muscle of four DMD patients injected with a 2'OMePS AO to exon 51 has been reported by van Deutekom et al.

One critical factor determining the effect of targeted removal of specific exon to restore dystrophin reading frame is the identification of specific antisense oligonucleotides Since antisense oligonucleotides normally have a sequence of only 20-30 nucleotides, there can be hundred or more potential candidate AOs for targeting each exon dystrophin exon. Practically, many antisense oligonucleotides do not produce efficient exon skipping. Therefore, to effectively remove an exon for the restoration of dystrophin reading frame for the treatment of DMD, antisense oligonucleotide targeting each human dystrophin exon needs to be screened and selected. However, there has been no roles to apply for the selection of most effective AO targeting individual exon. Further more, all previous arts identifies AOs which only show exon skipping effect in cell culture, which is hugely different from the final targeting cells of muscle fibers in patients of DMD. The biological effect of individual AO selected in cell culture could significantly different from the potential effect in muscle in vivo.

Accordingly, there still exists a need for improved antisense oligonucleotides which cause efficient exon skipping in targeted exons of the dystrophin gene.

BRIEF SUMMARY OF THE INVENTION

Embodiments of the present invention are directed generally to antisense compounds and compositions for the treatment of muscular dystrophy, and in particular, Duchenne muscular dystrophy (DMD).

In one embodiment, the invention is directed to antisense oligonucleotide molecules, pharmaceutical compositions and formulations comprising antisense oligonucleotide molecules, and methods of treating muscular dystrophy related diseases and disorders wherein the antisense oligonucleotide molecules comprises a base sequence selected from the group consisting of:

```
                                       (SEQ ID NO: 5)
       GCTGGGAGAGAGCTTCCTGTAGCTTCAC;

(SEQ ID NO: 6)
       TGTTACCTACCCTTGTCGGTCCTTGTAC;

(SEQ ID NO: 7)
       CTGCTGTCTTCTTGCTATGAATAATGTC;

(SEQ ID NO: 8)
       GGCGTTGCACTTTGCAATGCTGCTGTCT;

(SEQ ID NO: 10)
       TTGGAAATCAAGCTGGGAGAGAGCTTCC;

(SEQ ID NO: 12)
       CTACCCTTGTCGGTCCTTGTACATTTTG, (SEQ ID NO: 14)
       GTCAATCCGACCTGAGCTTTGTTGTAGA;

(SEQ ID NO: 16)
       CTTGCTATGAATAATGTCAATCCGACC;

(SEQ ID NO: 24)
       TATATGTGTTACCTACCCTTGTCGGTCC;

(SEQ ID NO: 27)
       GCCCAATGCCATCCTGGAGTTCCTG;

(SEQ ID NO: 28)
       CCAATGCCATCCTGGAGTTCCT;

(SEQ ID NO: 34)
       CCCAATGCCATCCTGGAGTTCCTGTAAGA;

(SEQ ID NO: 35)
       CCGCTGCCCAATGCCATCCTGGAGTTCC;

(SEQ ID NO: 37)
       CCCAATGCCATCCTGGAGTTCCTGTAAGAT;
```

-continued

```
                                            (SEQ ID NO: 40)
CCGCTGCCCAATGCCATCCTGGAGTTCCTG;

(SEQ ID NO: 42)
TGCCCAATGCCATCCTGGAGTTCCTGTAAG;

(SEQ ID NO: 44)
CCCAATGCCATCCTGGAGTTCCTGTAAG;

(SEQ ID NO: 45)
TGCCCAATGCCATCCTGGAGTTCCTGTA;

(SEQ ID NO: 46)
GCTGCCCAATGCCATCCTGGAGTTCCTG (SEQ ID NO: 79)
AACUUCCUCUUUAACAGAAAAGCAUAC;

(SEQ ID NO: 97)
GGGAUCCAGUAUACUUACAGGCUCC;

(SEQ ID NO: 100)
CTCCAACATCAAGGAAGATGGCATTTCT;

(SEQ ID NO: 101)
CATCAAGGAAGATGGCATTTCTAGT;
and (SEQ ID NO: 116)
CAACTGTTGCCTCCGGTTCTGAAG
``` and analogs and combinations thereof, and wherein the molecule can bind to a target site to cause exon skipping in the dystrophin gene. These sequences with one or 2 nucleotides less or more at the each end are expected to have similar effect, thus may also be used for targeted exon skipping in the dystrophin gene.

Further aspects of embodiments of the invention are directed to polymers for the enhanced cell delivery of antisense oligonucleotide molecules. In one embodiment, the present invention provides a class of polymers that are conjugates of poloxamer and polyethylemine (PEI). Poloxamer comprises a central hydrophobic chain of polyoxypropylene (poly(propylene oxide)) and two flanking hydrophilic chains of polyoxyethylene (poly(ethylene oxide).

BRIEF DESCRIPTION OF THE SEVERAL VIEWS OF THE DRAWING(S)

Figure 5:
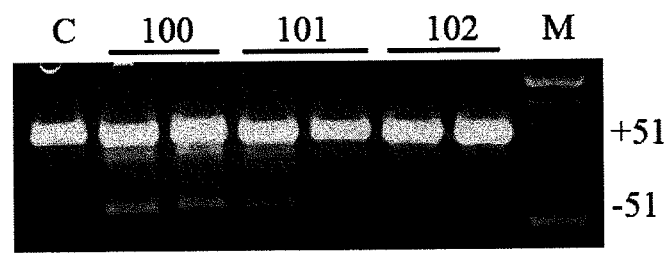
Figure 6:
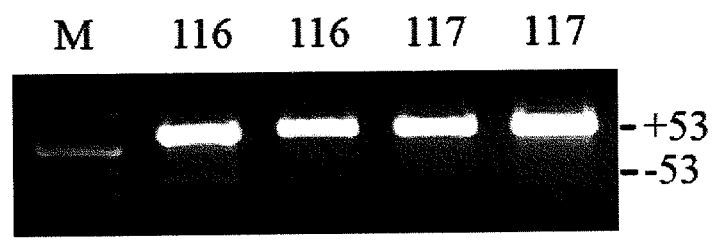
Figure 7:
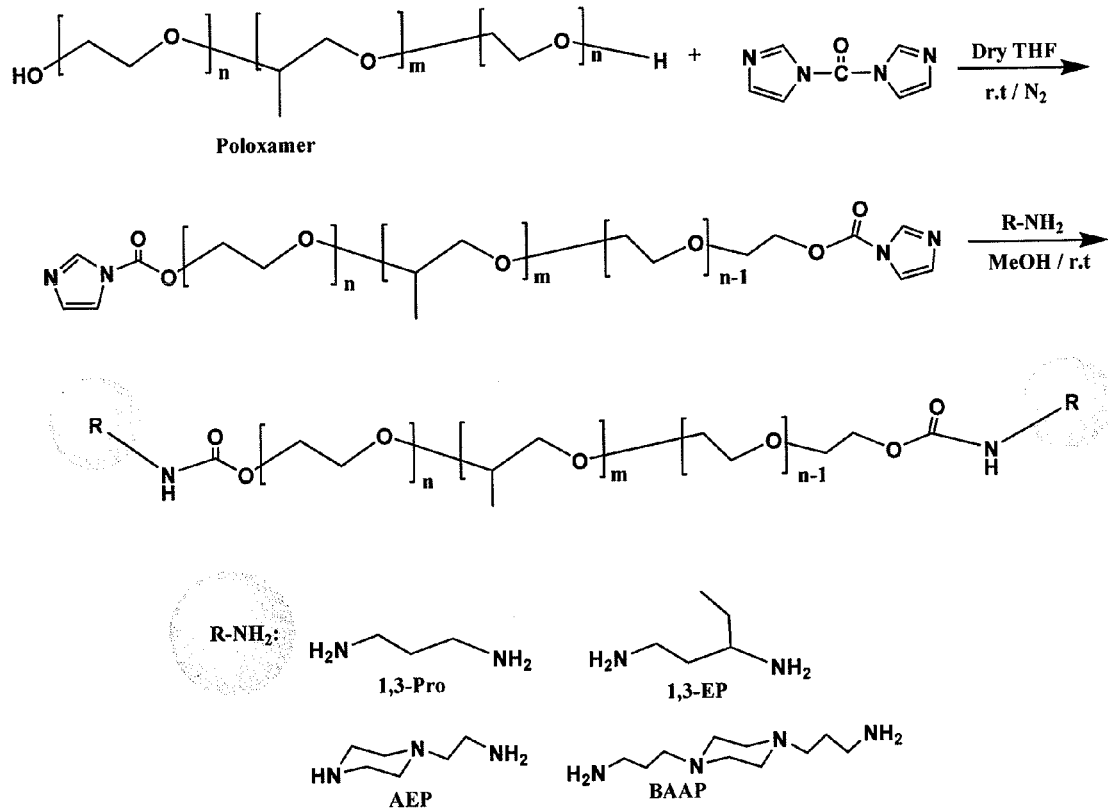

Having thus described the invention in general terms, reference will now be made to the accompanying drawings, which are not necessarily drawn to scale, and wherein:

FIGS. 1-6 are images of western blots that show skipping of various exons using antisense oligonucleotide molecules in accordance with embodiments of the present invention; and FIG. 7 shows structural chemistry of a polymer used in delivery of antisense oligonucleotide molecules in accordance with embodiments of the present invention.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention are directed to one or more antisense molecules that are capable of binding to specific targets to induce exon skipping. Certain embodiments of the present invention are also directed to methods of treating dystrophic related diseases including Duchenne muscular dystrophy (DMD).

Antisense molecules in accordance with embodiments of the present invention include oligonucleotide sequences that are capable of inducing exon skipping in the human dystrophin gene of at least one of exon 43, exon 45, exon 50, exon 51 and exon 53.

Desirably, antisense oligonucleotides in accordance with embodiments of the present invention have a high efficiency for inducing exon skipping in the targeted sequence. In one embodiment, antisense oligonucleotide molecules can cause an exon skipping at an efficiency of at least 20%, more preferably, at least 40%, even more preferably, at least 50%, more preferably still, at least 60%, more preferably, at least 80%.

In one embodiment, the present invention is directed to antisense oligonucleotide molecule that is capable of inducing exon skipping of exon 43 of the dystrophin gene. Antisense oligonucleotide molecules for targeting of exon 43 may include one or more of the following sequences and analogs thereof:

```
                                            (SEQ ID NO: 5)
GCTGGGAGAGAGCTTCCTGTAGCTTCAC;

(SEQ ID NO: 6)
TGTTACCTACCCTTGTCGGTCCTTGTAC;

(SEQ ID NO: 7)
CTGCTGTCTTCTTGCTATGAATAATGTC;

(SEQ ID NO: 8)
GGCGTTGCACTTTGCAATGCTGCTGTCT;

(SEQ ID NO: 10)
TTGGAAATCAAGCTGGGAGAGAGCTTCC;

(SEQ ID NO: 12)
CTACCCTTGTCGGTCCTTGTACATTTTG, (SEQ ID NO: 14)
GTCAATCCGACCTGAGCTTTGTTGTAGA;

(SEQ ID NO: 16)
CTTGCTATGAATAATGTCAATCCGACC;
and (SEQ ID NO: 24)
TATATGTGTTACCTACCCTTGTCGGTCC.
```

In a further embodiment, the present invention is directed to antisense oligonucleotide molecule that is capable of inducing exon skipping of exon 45 of the dystrophin gene. Antisense oligonucleotide molecules for targeting of exon 45 in accordance with the present invention may include one or more of the following sequences and analogs thereof:

```
                                            (SEQ ID NO: 27)
GCCCAATGCCATCCTGGAGTTCCTG;

(SEQ ID NO: 28)
CCAATGCCATCCTGGAGTTCCT;

(SEQ ID NO: 34)
CCCAATGCCATCCTGGAGTTCCTGTAAGA;

(SEQ ID NO: 35)
CCGCTGCCCAATGCCATCCTGGAGTTCC;
```

```
                                                  (SEQ ID NO: 37)
CCCAATGCCATCCTGGAGTTCCTGTAAGAT;

(SEQ ID NO: 40)
CCGCTGCCCAATGCCATCCTGGAGTTCCTG;

(SEQ ID NO: 42)
TGCCCAATGCCATCCTGGAGTTCCTGTAAG;

(SEQ ID NO: 44)
CCCAATGCCATCCTGGAGTTCCTGTAAG;

(SEQ ID NO: 45)
TGCCCAATGCCATCCTGGAGTTCCTGTA;
and (SEQ ID NO: 46)
GCTGCCCAATGCCATCCTGGAGTTCCTG.
```

In yet another embodiment, the present invention is directed to antisense oligonucleotide molecule that is capable of inducing exon skipping of exon 50 of the dystrophin gene. Antisense oligonucleotide molecules in accordance with embodiments of the present invention for targeting of exon 50 may include one or more of the following sequences and analogs thereof:

```
                                                  (SEQ ID NO: 79)
AACUUCCUCUUUAACAGAAAAGCAUAC;
and (SEQ ID NO: 97)
GGGAUCCAGUAUACUUACAGGCUCC.
```

Embodiments of the present invention are also directed to antisense oligonucleotide molecule that is capable of inducing exon skipping of exon 51 of the dystrophin gene. Antisense oligonucleotide molecules for targeting of exon 51 may include one or more of the following sequences and analogs thereof:

```
                                                  (SEQ ID NO: 100)
CTCCAACATCAAGGAAGATGGCATTTCT;
and (SEQ ID NO: 101)
CATCAAGGAAGATGGCATTTCTAGT.
```

Embodiments of the present invention are also directed to antisense oligonucleotide molecule that is capable of inducing exon skipping of exon 53 of the dystrophin gene. Antisense oligonucleotide molecules for targeting of exon 53 may include one or more of the following sequences and analogs thereof:

```
                                                  (SEQ ID NO: 116)
CAACTGTTGCCTCCGGTTCTGAAG.
```

It should also be recognized that the present invention also includes analogs of the aforementioned oligonucleotide sequences. In the present invention, the term "analogs" of the inventive oligonucleotide sequences may include sequences in which one or more thymine (T) bases have been substituted for uracil (U) base and vice versa. For instance, the presence of either base in a sequence generally still allows for the molecule to bind to the pre-mRNA of the dystrophin gene as it is a complementary sequence. Therefore, the presence of either base in the molecule will generally induce exon skipping. The above sequences of the molecule may contain all thymines, all uracils or a combination of the two. As is known to one of the art, the selection of T or U in the sequences may be based, at least in part on the chemistry used to produce the molecule. For example, if the molecule is a phosphorodiamidate morpholino oligonucleotide (PMO), X may desirably be T as this base is used when producing PMOs. Alternatively, if the molecule is a phosphorothioate-linked 2'-O-methyl oligonucleotide (2'OMePS), X may desirably be U as this base is used when producing 2'OMePSs.

Additional analogs of the inventive oligonucleotide sequences may include sequences in which up to two of the bases have been deleted or substituted with other bases provided the molecule is capable of inducing exon skipping of the targeted exon. Further analogs in accordance with the present invention may include oligonucleotide sequences having an additional base added to one or both ends of the sequence, or in which one base at one or more of the opposite ends of the sequence have been deleted. For example, analogs of CTGCTGTCTTCTTGCTATGAATAATGTC (SEQ ID NO. 7) may include the following:

```
                                                  (SEQ ID NO 119)
XCTGCTGTCTTCTTGCTATGAATAATGTCX'
``` where X and X' are independently are one of C, T, G, U, and A;

```
                                                  (SEQ ID NO 120)
TGCTGTCTTCTTGCTATGAATAATGTC (SEQ ID NO 121)
CTGCTGTCTTCTTGCTATGAATAATGT;
and (SEQ ID NO 122)
TGCTGTCTTCTTGCTATGAATAATGT.
```

Antisense oligonucleotide molecules in accordance with the present invention can be any type of molecule as long as it has the selected base sequence and can bind to a target site of the dystrophin pre-mRNA to cause exon skipping. For example, the molecule can be an oligodeoxyribonucleotide, an oligoribonucleotide, a phosphorodiamidate morpholino oligonucleotide (PMO) or a phosphorothioate-linked 2'-O-methyl oligonucleotide (2'OMePS). Preferably, the oligonucleotide is a PMO. Preferably, the molecule is isolated so that it is free from other compounds or contaminants.

In one embodiment, the antisense oligonucleotide molecules in accordance with the present invention include PMO and peptide nucleic acids (PNA). Morpholino oligomers are polymeric molecules having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains (a ring nitrogen with coupling through the ring nitrogen). Examples of suitable morpholino oligomers include phosphorodiamidate morpholino oligomer Examples of morpholino oligomers that may be used in the practice of the present invention are described in greater detail in U.S. Pat. Nos. 5,698,685, 5,217,866, 5,142, 047, 5,034,506, 5,166,315, 5,185,444, 5,521,063, 5,506,337, 6,124,271, 6,784,291, 7,049,431, 7,582,615, and 7,625,873.

Peptide nucleic acid polymers (PNA) can also be used as antisense oligomers in the practice of the invention. PNA has the backbone structurally homomorphous with the deoxyribose backbone and consists of N-(2-aminoethyl)glycine units where the nucleobases are attached. PNA has been investigated as antisense oligomers for the potential of targeting genes related to human diseases. The easy synthesis of PNA together with positively charged polymers has lead PNA and its conjugates being widely tested as drugs of experimental therapy to cancers, genetic disorders and other diseases.

In certain embodiments, antisense oligonucleotide molecules, and in particular, morpholino oligomers and PNAs, in accordance with the present invention can be conjugated with a wide variety of different positively charged polymers. Examples of positively charged polymers include peptides, such as argine rich peptides (Examples of positively charged peptides that may be used in the practice of the invention include R9F2C; $(RXR)_4$ XB (where X can be any amino acid); R5F2R4c; $(RFF)_3$; Tat proteins, such as TAT sequence CYGRKKRRQRRR; and $(RFF)_3R$), cationic polymers, such as dendrimeric octaguanindine polymer, and other positively charged molecules as known in the art for conjugation to antisense oligonucleotide compounds. In one embodiment, the antisense oligonucleotides are conjugated with positively charged polymer comprising a polymer having a molecular weight that is from about 1,000 to 20,000 Daltons, and preferably from about 5,000 to 10,000 Daltons. Another example of positively charged polymers is polyethylenimine (PEI) with multiple positively charged amine groups in its branched or unbranched chains. PEI has else been widely used as gene and oligomer delivery vesicle.

Embodiments of the present invention are also directed to pharmaceutical formulations and compositions for the treating of DMD, and in particular, ameliorating the effects of DMD. Treatment" or "treating" of an individual (e.g., a mammal, such as a human) or a cell may include any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition associated with the dystrophin protein, as in certain forms of muscular dystrophy, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

In particular, are included methods of treating muscular dystrophy, such as DMD and BMD, by administering one or more antisense oligonucleotides of the present invention (e.g., SEQ ID NOS: 5-8, 10, 12, 14, 16, 24, 27, 28, 34, 35, 37, 40, 42, 44, 45, 46, 79, 97, 100, 101, and 116, and analogs and combinations thereof), optionally as part of a pharmaceutical formulation or dosage form, to a subject in need thereof. Also included are methods of inducing exon-skipping in a subject by administering one or more antisense oligomers, in which the exon is one of exons 42, 44, 45, 50, 51, and 53, and combinations thereof from the human dystrophin gene. A "subject," as used herein, includes any animal that exhibits a symptom, or is at risk for exhibiting a symptom, which can be treated with an antisense compound of the invention, such as a subject that has or is at risk for having DMD or BMD, or any of the symptoms associated with these conditions (e.g., muscle fiber loss). Suitable subjects (patients) include laboratory animals (such as mouse, rat, rabbit, or guinea pig), farm animals, and domestic animals or pets (such as a cat or dog) as long as such subjects contain the complementary sequences of the invention. Non-human primates and, preferably, human patients, are included.

Pharmaceutical formulations comprising antisense oligonucleotide molecules in accordance with the present invention may be administered in any convenient physiologically acceptable vehicle. Examples of standard pharmaceutically accepted carriers include saline, phosphate buffered saline (PBS), water, aqueous ethanol, emulsions such as oil/water emulsions, triglyceride emulsions, wetting agents, tablets and capsules. It should be recognized that the choice of suitable physiologically acceptable carrier will vary dependent upon the chosen mode of administration.

In one embodiment, the pharmaceutical composition may comprise a plurality of molecules of the invention, each molecule directed to exon skipping in a different exon. Alternatively, the pharmaceutical composition may comprise a plurality of molecules of the invention, each molecule directed to exon skipping in the same exon.

The pharmaceutical compositions of the present invention may be provided to target cells by any suitable means, including direct administration (e.g., in vitro by addition to culture medium, or in animals in vivo locally by injection or topical administration at a treatment site) or systemically (e.g., parenterally or orally, or intravenously, subcutaneously). In one embodiment, the compounds and compositions comprise part of a physiologically acceptable solution so that in addition to delivery of the desired agent to the target cells, the solution does not otherwise adversely affect the electrolyte and/or volume and/or metabolism of the cells or tissue or subject.

The pharmaceutical compositions and compounds as utilized in this invention can be administered by intranasal, oral, inhalational, enteral, topical, intrauterine, vaginal, sublingual, rectal, intramuscular, intrapleural, intraventricular, intraperitoneal, ophthalmic, intravenous, or subcutaneous means. In a preferred embodiment, the pharmaceutical solution is provided via an intravenous injection.

Pharmaceutical compositions in accordance with the present invention may be supplied in liquid or solid form. Compositions in accordance with the present invention may further include solvents, diluents, excipients, preservatives, emulsifiers, compounds for adjusting odor, taste, pH or the like. In general, in addition to the active compounds, the pharmaceutical compositions of the invention may contain suitable excipients and auxiliaries which facilitate processing and delivery of the active compounds into preparations which can be used pharmaceutically. Suitable excipients include fillers such as sugars, for example, lactose, sucrose, mannitol or sorbitol, cellulose preparations, calcium phosphates, and binders such as starch, gelatin, methyl cellulose, hydroxypropyl methylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, alginic acid, or a salt thereof. Auxiliaries include flow-regulating agents and lubricants, for example, silica, talc, stearic acid or salts thereof, and/or polyethylene glycol.

The formulations can be administered with or without additional carrier or diluent by the oral, systemic injections, percutaneous, transmucosal, or other typical route. Pharmaceutical formulations in accordance with the present invention may be administered orally in caplet, tablet, particle, granule, or powder forms.

The present invention also provides a method of treating and/or ameliorating the effects one or more medical conditions by administering a therapeutically effective amount and/or a prophylactic amount of the aforementioned pharmaceutical formulations, to a sufferer in need thereof. According to the present invention, a "therapeutically effective amount" of a compound, combination or pharmaceutical composition of the invention is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect.

Typical dosage amounts of the antisense oligonucleotide molecules in pharmaceutical formulations may range from about 0.05 to 1000 mg/kg body weight, and in particular from about 5 to 500 mg/kg body weight. In one embodiment, the dosage amount is from about 50 to 300 mg/kg body weight once in 2 weeks, or once or twice a week, or any frequency required to achieve therapeutic effect.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment, dosage forms (compositions) of the inventive pharmaceutical composition may contain about 1 microgram to 20,000 micrograms of active ingredient per unit, and in particular, from about 10 to 1000 micrograms of active ingredient per unit.

(if here a unit means a vial or one package for one injection, then it will be much higher, up to 15 g if the weight of a patient is 50 kg) For intravenous delivery, a unit dose of the pharmaceutical formulation will generally contain from 0.5 to 500 micrograms per kg body weight and preferably will contain from 5 to 300 micrograms, in particular 10, 15, 20, 30, 40, 50, 100, 200, or 300 micrograms per kg body weight (μg/kg body weight) of the antisense oligonucleotide molecule. Preferred intravenous dosage ranges from 10 ng to 2000 μg, preferably 3 to 300 μg, more preferably 10 to 100 μg of metal per kg of body weight. Alternatively the unit dose may contain from 2 to 20 micrograms of the antisense oligonucleotide molecule and be administered in multiples, if desired, to give the preceding daily dose. In these pharmaceutical compositions, the antisense oligonucleotide molecule will ordinarily be present in an amount of about 0.5-95% by weight based on the total weight of the composition.

In one particular embodiment, it should be recognized that the dosage can be raised or lowered based on individual patient response. It will be appreciated that the actual amounts of antisense oligonucleotide molecule used will vary according to the specific antisense oligonucleotide molecule being utilized, the particular compositions formulated, the mode of application, and the particular site of administration.

For oral administration when the composition is in the form of a tablet or capsule, the active ingredient can be combined with an oral, non-toxic, pharmaceutically acceptable, inert carrier, including but not limited to, lactose, starch, sucrose, glucose, methyl cellulose, magnesium stearate, dicalcium phosphate, calcium sulfate, mannitol, sorbitol and the like. Additionally, when desired or necessary, suitable binders, lubricants, disintegrating agents, and coloring agents can also be incorporated into the mixture. Suitable binders may include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms may include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In some embodiments, antisense oligonucleotide molecules formulations of the present invention may also be coupled with soluble polymers as targetable drug carriers. Such polymers can include, for example, polyvinylpyrrolidone, pyran copolymer, polyhydroxypropylmethacrylamidephenol, polyhydroxyethylaspartamidephenol, or polyethyleneoxide-polylysine substituted with palmitoyl residues, or Poloxamer and Polyethylemine (PEI), or a conjugated polymer of Poloxamer and PEI. The Poloxamer can be any such as L44, L64, P85, P123 and F127. In this regard, FIG. 7 shows a polymer that can be used for cell delivery in accordance with certain embodiments of the present invention.

In one embodiment, antisense oligonucleotide molecule formulations in accordance with the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, a conjugated polymer of Poloxamer and PEI and crosslinked or amphipathic block copolymers of hydrogels.

The compositions described herein may be administered as part of a sustained-release formulation (i.e., a formulation such as a capsule or resin or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane. Carriers for use within such formulations are biocompatible, and may also be biodegradable; preferably the formulation provides a relatively constant level of modulating agent release.

It is noted that humans are generally treated longer than mice or other experimental animals exemplified herein. Accordingly, the length of the treatment generally may be proportional to the length or intensity or prior duration of the disease or pathophysiological process, and may further depend on the animal species, drug effectiveness and degree of effect required or recommended. The doses may be single doses or multiple doses over a period of one day, one week, one year to entire life span.

In one embodiment, the pharmaceutical compositions and compounds of the present invention are administered topically, especially when the target of treatment includes areas or organs readily accessible by topical application, including diseases of the eye, the skin, or the lower intestinal tract. Topical application may also be readily used to administer the combinations, compounds and compositions of the invention to tissue below the skin, such as muscle. Suitable topical formulations may be prepared for each of these areas or organs.

Topical application for the lower intestinal tract may be effected in a rectal suppository formulation or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

Formulations suitable for topical administration to the eye also include eye drops wherein the active ingredients were dissolved or suspended in a suitable carrier, especially an aqueous solvent for the active ingredients. The active ingredients were preferably present in such formulations in a concentration of 0.5 to 20%, advantageously 0.5 to 10% and particularly about 1.5% w/w.

One can use topical administration to deliver a pharmaceutical formulation of the invention by percutaneous passage of the active agents into the systemic circulation of the patient. The skin sites include anatomic regions for transdermally administering the drug, such as the forearm, abdomen, chest, back, buttock, thigh and retroauricular area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin, or the formulation is applied directly on the skin in a prescribed amount and schedule.

Formulations suitable for topical administration include liquid or semi-liquid preparations suitable for penetration through the skin (e.g., liniments, lotions, ointments, creams, gels or pastes) and drops suitable for administration to the eye, ear, or nose. A suitable topical dose of active ingredient of a compound of the invention is expected to be similar to the dose used by any other local and systemic route When formulated in an ointment, the antisense oligonucleotides may be employed with either paraffinic or a water-miscible ointment base. Alternatively, the antisense oligonucleotides may be formulated in a cream with an emulsified cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include methocarbamol, longer-chain alcohols, dimethylsulfoxide and related analogs.

A variety of transdermal drug delivery devices can be employed with the pharmaceutical formulations of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating.

Transdermal administration may be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, flavoring agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, flavoring agents, coloring agents, and the like.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include TWEEN™ 60, SPAN™ 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents, as well as anti-fungal agents. Perfumes or volatile agents that confer an odour on the composition while, by evaporating, they 'set' or dry a topical formulation/application, may also be included.

The pharmaceutical compositions of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption.

In one embodiment, the method is carried out by administering to the subject an antisense oligonucleotide, and in particular a morpholino oligomer that is selected to target a specific gene region aiming to restore specific gene expression or switch the isoforms of the gene. In general, the method comprises administering to a subject, in a suitable pharmaceutical carrier, an amount of the antisense oligonucleotide molecule effective to interfere with the integrety, transcription or splicing, and thus suppress or restore normal expression of the protein, or switch the expression of different isoforms. In a preferred embodiment, the method results in expression of a dominant negative variant of the protein. In one aspect of the method, the subject is a human subject. For use in antiviral treatment, various systemic routes of delivery, including oral and parenteral routes, e.g., intravenous, subcutaneous, intraperitoneal, and intramuscular, as well as inhalation, transdermal and topical delivery, can be used.

Typically, one or more doses of antisense oligonucleotide molecules are administered, generally at regular intervals, preferably once a day to once a month. Preferred doses for oral administration are from about 1 mg per kg of bodyweight antisense oligonucleotide molecule to about 600 mg antisense oligonucleotide molecule per kg body weight, and more preferably, from about 30 mg per kg of bodyweight antisense oligonucleotide molecule to about 300 mg antisense oligonucleotide molecule per kg body weight. For IV administration, the preferred doses are similar to the doses described above. Dosages will vary in accordance with such factors as the age, health, sex, size and weight of the patient, the route of administration, and the efficacy of the antisense oligonucleotide molecule with respect to the particular disease state.

An effective in vivo treatment regimen using the antisense oligonucleotides of the invention will vary according to the frequency and route of administration, as well as the condition of the subject under treatment. Optimum dosages for a given route can be determined by routine experimentation according to methods known in the art. Such in vivo therapy is generally monitored by tests appropriate to the particular type of ailment being treated, and a corresponding adjustment in the dose or treatment regimen can be made in order to achieve an optimal therapeutic outcome.

In another aspect, the invention provides a kit for the amelioration of DMD in a patient, the kit comprising a molecule of the invention and instructions for its use. In one embodiment, the kit may contain a plurality of molecules for use in causing exon skipping in the same exon or a plurality of exons.

EXAMPLES

In the following Examples, three different in vitro and in vivo models were utilized to test the efficacy of the antisense oligonucleotide molecules: 1) DMD myoblast; 2) normal human myoblast; and 3) humanized DMD (hDMD) mice (containing the entire human dystrophin gene which expresses near normal levels of dystrophin). The three models were used to screen antisense oligomers targeting the specific human dystrophin exons.

The DMD myoblasts and normal human myoblasts were grown in 24 well plates and 2.5 µM PMO or 2'-O-methyl oligonucleotide (2'OMePS) was used for initial screening in duplicate for each antisense oligonucleotide. 24 hours after AO treatment, the cells were then cultured in differentiation medium for further 2 days.

For tests in hDMD mouse, 20 µg PMO antisense oligonucleotides were prepared in 40 µl saline and administrated by intramuscular injections in duplicates. The antisense oligonucleotides were delivered together with polymers comprising conjugates of poloxamer and polyethylemine (PEI), or PMOs conjugated with dendrimeric octaguanindine polymer to aid in muscle fiber delivery. Poloxamer comprises a central hydrophobic chain of polyoxypropylene (poly(propylene oxide)) and two flanking hydrophilic chains of polyoxyethylene (poly(ethylene oxide). In this regard, FIG. 7 depicts a chemical structure of the polymers used for the delivery of PMO in cell culture and in vivo in the hDMD mice. These polymers are conjugates of the Poloxamer and Polyethylemine (PEI). Poloxamer is composed of a central hydrophobic chain of polyoxypropylene (poly(propylene oxide)) and two flanking hydrophilic chains of polyoxyethylene (poly(ethylene oxide) with the MW of 1000 to 15000. They can be any of the followings, L44, L64, P85, P123 and F127. The molecular weight (MW) of PEI may vary from 400 to 2000.

Treated muscles were harvested 7 days after single injection and the muscles were snap-frozen in liquid nitrogen-cooled isopentane and stored at −80° C. Sections were cut from the muscles and collected into microcentrafuge tubes and then RNAs were extracted for RT-PCR.

Exon skipping efficiency in each model system was determined by RT-PCR and Nested-PCR in DMD-derived cells and human myoblasts and by RT-PCR in hDMD mice. The following procedures were used: RNA from oligomer-treated cells or muscle tissues was extracted with TriZol reagent (Invitrogene, Carlsbad, Calif.) according to manufacturer's instructions. RNA was stored at −80° C. for later use. RT-PCR was performed with RT-Fidelitaq MasterMix (USB, Cleveland, Ohio) to amplify the sequence of interest. 100 ng of template RNA was used for each 250 RT-PCR reaction. The PCR conditions were 43° C. for 15 minutes, 94° C. for 2 minutes, then cycled 30 times at 94° C. for 30 seconds, 65° C. for 30 seconds, and 68° C. for 1 minute. The conditions for nested PCR were 94° C. for 2 minutes, then cycled 30 times at 94° C. for 30 seconds, 55° C. for 30 seconds, 72° C. for 1 minute, and 72° C. for 5 minutes.

The following pairs of primers were used for the RT-PCR and nested PCR:

```
RT-PCR primers 1:
Forward primer: Ex47/48F3, 5'-GTGGATAAAGGTTTCCAGAGC-3'

Reverse primer Ex53/52R3, 5'-GAATTCTTTCAATTCGATCCGTA-3'.

Nested PCR primers 1:
Forward primer: Ex48F2, 5'-TCTGCTGCTGTGGTTATCTC-3';

Reverse primer: Ex52R2, 5'-TTTTGGGCAGCGGTAATGAG-3'.

RT-PCR primers 2:
Forward primer: E43F6206/6230, 5'-TGGAAAGGGTGAAGCTACAGGAAG-3'

Reverse primer: E46-47R6780/6775 5'-CAACTCTTCCACCAGTAACTTGACT-3'

Nested PCR primers 2:
Forward primer E43F6265/6290, 5'-AACAAAATGTACAAGGACCGACAAGG-3'

Reverse primer E46R6732/6708, 5'-CTGCTCTTTTCCAGGTTCAAGTGG-3'

RT-PCR primers 3:
Forward primer: E43F6206/6230, 5'-TGGAAAGGGTGAAGCTACAGGAAG-3'

Reverse primer: E49R7111/7137, 5'- CACATCCGGTTGTTTAGCTTGAACTGC -3'

Nested PCR primers 3:
Forward primer: E43F6265/6290, 5'-AACAAAATGTACAAGGACCGACAAGG-3'

Reverse primer: E48R7034/7017, 5'-CTAATAGGAGATAACCACAGCAGCAGA-3'.

RT-PCR primers 4:
hDysEx41F1: GGGAAATTGAGAGCAAATTTGC;

hDysEx45R1: GAGGATTGCTGAATTATTTCTTCC.

Nested PCR primers 4:
hDysEx41/42F2: CAACTTTGCACAAATTCACAC;

hDysEx45R2: CAATGTTCTGACAACAGTTTGCCG.
```

The PCR products were examined by electrophoresis on a 2% agarose gel. The intensity of the PCR products demonstrated by the Ethidium bromide staining was measured with NIH image J 1.42 software.

In general, the PCR product representing the mRNA with the targeted exon skipped will be compared to the PCR product representing the mRNA without skipping of the targeted exon. The total signal intensity from the 2 bands will be considered 100%. Therefore, exon skipping efficiency will be considered 50% if the signal intensity of the transcript with targeted exon skipped is equal to that of normal mRNA without exon skipping. Another example is that exon skipping efficiency will be considered 90% if the signal intensity of the transcript with targeted exon skipped is 90% of total signal intensity representing both transcripts with and without the targeted exon skipped.

The results for the antisense oligonucleotide sequences that were prepared and evaluated are summarized in the tables below.

TABLE 1

| AO SEQUENCES TARGETING EXON 43 | | | | | | |
|---|---|---|---|---|---|---|
| Antisense | | | skipping efficiency (%) | | | SEQ |
| oligonucleotide name | Sequences (5' to 3') | Length (bp) | Human Myoblast | DMD Myoblast | HDMD Mice | ID No. |
| HE43 (−1 +27) | GCTTTGTTGTAGACTATCTTTTATATTC | 28 | 75 | 60* | 15 | 1 |
| HE43 (+9 +36) | CCGACCTGAGCTTTGTTGTAGACTATCT | 28 | 80 | 100** | 12.5 | 2 |
| HE43 (+85 +112) | CTTCCTGTAGCTTCACCCTTTCCACAGG | 28 | 15 | 40 | 15 | 3 |
| HE43 (+97 +124) | GCTGGGAGAGAGCTTCCTGTAGCTTCAC | 28 | 10 | 50* | 2.5 | 4 |
| HE43 (+156 −10) | TGTTACCTACCCTTGTCGGTCCTTGTAC | 28 | 45 | 40 | 40 | 5 |
| HE43 (+26 +53) | CTATGAATAATGTCAATCCGACCTGAGC | 28 | 85 | 40* | 50 | 6 |
| HE43 (+40 +67) | CTGCTGTCTTCTTGCTATGAATAATGTC | 28 | 80 | 48* | 55 | 7 |

TABLE 1-continued

AO SEQUENCES TARGETING EXON 43

| Antisense oligonucleotide name | Sequences (5' to 3') | Length (bp) | skipping efficiency (%) Human Myoblast | DMD Myoblast | HDMD Mice | SEQ ID No. |
|---|---|---|---|---|---|---|
| HE43(+59 +86) | GGCGTTGCACTTTGCAATGCTGCTGTCT | 28 | 35 | 48* | 40 | 8 |
| HE43(+108 +135) | TTGGAAATCAAGCTGGGAGAGAGCTTCC | 28 | 10 | 48* | 22.5 | 9 |
| HE43(+118 +145) | CTTTTTCCCATTGGAAATCAAGCTGGGA | 28 | 50 | 40 | .5 | 10 |
| HE43(+142 +169) | GTCGGTCCTTGTACATTTTGTTAACTTT | 28 | 10 | 0 | 2.5 | 11 |
| HE43(+150 -4) | CTACCCTTGTCGGTCCTTGTACATTTTG | 28 | 75 | 48* | 15 | 12 |
| HE43(+7 +34) | GACCTGAGCTTTGTTGTAGACTATCTTT | 28 | 40 | 30 | 0 | 13 |
| HE43(+14 +42) | GTCAATCCGACCTGAGCTTTGTTGTAGA | 28 | 30 | 40 | 50 | 14 |
| HE43(+19 +46) | TAATGTCAATCCGACCTGAGCTTTGTTG | 28 | 25 | 5 | 20 | 15 |
| HE43(+31 +57) | CTTGCTATGAATAATGTCAATCCGACC | 27 | 45 | 5 | 30 | 16 |
| HE43(+35 +62) | GTCTTCTTGCTATGAATAATGTCAATCC | 28 | 30 | 10 | 25 | 17 |
| HE43(+53 +80) | GCACTTTGCAATGCTGCTGTCTTCTTGC | 28 | 35 | 5 | 5 | 18 |
| HE43(+64 +91) | CCACAGGCGTTGCACTTTGCAATGCTGC | 28 | 10 | 100 | 10 | 19 |
| HE43(+77 +104) | AGCTTCACCCTTTCCACAGGCGTTGCAC | 28 | 40 | 45 | 10 | 20 |
| HE43(+78 +100) | TCACCCTTTCCACAGGCGTTGCA | 23 | 40 | 95 | 10 | 21 |
| HE43(+101 +120) | GGAGAGAGCTTCCTGTAGCT | 20 | 20 | 95 | 10 | 22 |
| HE43(+113 +140) | TCCCATTG GAAATCAAGCTGGGAGAGAG | 28 | 10 | 50 | 5 | 23 |
| HE43(+162 -16) | TATATGTGTTACCTACCCTTGTCGGTCC | 28 | 65 | 40 | 45 | 24 |

*showed transcripts with deletion of both exon 43 and exon 44 as well as transcript with deletion of exon 43 only.
**high levels of transcripts with deletion of both exon 43 and exon 44 as well as transcript with deletion of exon 43 only. Discrepancy in efficiency of targeted exon skipping with individual AO sequence between in cell culture and in muscle in vivo is clearly present. In one embodiment, preferred AO sequences for targeting dystrophin exon 43 include HE43(+30156-10), HE43(+3026+3053), HE43(+40 +67), HE43(+14 +42), HE43(+31 +57) HE43(+108+135), HE43(+150-4), HE43(+59+86), HE43(+162 -16); SEQ. ID NOs 5, 6,7, 8, 14, 16 and 24, with exon skipping efficiency reach 30% or higher in the muscle in vivo.

FIG. 1 shows a series of western blots of in vivo exon 43 skipping with 24 AOs in the hDMD mice by i.m. injection of 20 μg PMO in conjunction with the use of delivery-enhancing polymer. Exon 43 skipping was detected by RT-PCR. C, control without AO treatment. +43, represents transcripts without exon 43 skipping and −43 represents transcripts with exon 43 skipping. As can be seen in FIG. 1, high levels of exon skipping was obtained with AO 6, 7, 8, 14, 15, 16, 17, 24.

TABLE 2

AO SEQUENCES TARGETING EXON 45

| Antisense oligonucleotide name | Sequences (5' to 3') | Length (bp) | skipping efficiency (%) Human Myoblast | DMD Myoblast | HDMD Mice | SEQ ID No. |
|---|---|---|---|---|---|---|
| HE45 (-12 +15) | GCCATCCTGGAGTTCCTGTAAGATACC | 27 | 81.4 | <10 | 17.8 | 25 |
| HE45 (-19 +6) | GAGTTCCTGTAAGATACCAAAAAGG | 25 | 59.4 | <10 | 0 | 26 |
| HE45(-3 +22) | GCCCAATGCCATCCTGGAGTTCCTG | 25 | 33.6 | 63.8 | 59.6 | 27 |
| HE45(-2 +20) | CCAATGCCATCCTGGAGTTCCT | 22 | 51.4 | 58.1 | 57.2 | 28 |
| HE45(-6 +18) | AATGCCATCCTGGAGTTCCTGTAA | 24 | 59.1 | 76.5 | 0 | 29 |

TABLE 2-continued

AO SEQUENCES TARGETING EXON 45

| Antisense oligonucleotide name | Sequences (5' to 3') | Length (bp) | skipping efficiency (%) Human Myoblast | DMD Myoblast | HDMD Mice | SEQ ID No. |
|---|---|---|---|---|---|---|
| HE45(-15 +10) | CCTGGAGTTCCTGTAAGATACCAAA | 25 | 9 | <5 | — | 30 |
| HE45(-9 +16) | TGCCATCCTGGAGTTCCTGTAAGAT | 25 | 10.5 | <5 | — | 31 |
| HE45(-11 +11) | TCCTGGAGTTCCTGTAAGATAC | 21 | 27.8 | <5 | — | 32 |
| HE45(-11 +14) | CCATCCTGGAGTTCCTGTAAGATAC | 25 | 67.2 | <5 | — | 33 |
| HE45(-8 +21) | CCCAATGCCATCCTGGAGTTCCTGTAAGA | 29 | 54.5 | 52.1 | 61.3 | 34 |
| HE45(-1 +27) | CCGCTGCCCAATGCCATCCTGGAGTTCC | 28 | 66.6 | 72.1 | 55.1 | 35 |
| HE45(-11 +19) | CAATGCCATCCTGGAGTTCCTGTAAGATAC | 30 | 93.4 | <5 | 0 | 36 |
| HE45(-9 +21) | CCCAATGCCATCCTGGAGTTCCTGTAAGAT | 30 | 88.2 | 16 | 60 | 37 |
| HE45(-2 +28) | GCCGCTGCCCAATGCCATCCTGGAGTTCCT | 30 | 38.7 | 42.8 | 0 | 38 |
| HE45(-12 +18) | AATGCCATCCTGGAGTTCCTGTAAGATACC | 30 | 25.8 | <5 | — | 39 |
| HE45(-3 +27) | CCGCTGCCCAATGCCATCCTGGAGTTCCTG | 30 | 54.4 | <10 | 44.2 | 40 |
| HE45(-1 +29) | TGCCGCTGCCCAATGCCATCCTGGAGTTCC | 30 | 24.5 | 32.5 | 0 | 41 |
| HE45(-7 +23) | TGCCCAATGCCATCCTGGAGTTCCTGTAAG | 30 | 17 | <5 | 64.1 | 42 |
| HE45(-9 +19) | CAATGCCATCCTGGAGTTCCTGTAAGAT | 28 | 41.6 | <5 | 0 | 43 |
| HE45(-7 +21) | CCCAATGCCATCCTGGAGTTCCTGTAAG | 28 | 24.3 | 81.2 | 42.8 | 44 |
| HE45(-5 +23) | TGCCCAATGCCATCCTGGAGTTCCTGTA | 28 | 63.2 | 88.4 | 23 | 45 |
| HE45(-3 +25) | GCTGCCCAATGCCATCCTGGAGTTCCTG | 28 | 27.3 | 95.4 | 21 | 46 |
| HE45(12 +13) | CATCCTGGAGTTCCTGTAAGATACC | 25 | <10 | <10 | — | 47 |
| HE45(-12 +15) | GCCATCCTGGAGTTCCTGTAAGATACC | 27 | <10 | <10 | — | 48 |
| E45 +1 +25 | GCTGCCCAATGCCATCCTGGAGTTC | 25 | <10 | <10 | — | 49 |
| E45 +3 +22 | GCCCAATGCCATCCTGGAGT | 20 | <10 | <10 | — | 50 |
| E45 +5 +29 | TGCCGCTGCCCAATGCCATCCTGGA | 25 | <10 | <10 | — | 51 |
| E45 +6 +24 | CTGCCCAATGCCATCCTGG | 19 | <10 | <10 | — | 52 |
| E45 +9 +34 | CAGTTTGCCGCTGCCCAATGCCATCC | 26 | <10 | <10 | — | 53 |
| E45 +12 +35 | ACAGTTTGCCGCTGCCCAATGCCA | 24 | <10 | <10 | — | 54 |
| E45 +17 +41 | CTGACAACAGTTTGCCGCTGCCCAA | 25 | 20.9 | 20.9 | — | 55 |
| E45 +34 +53 | GCATTCAATGTTCTGACAAC | 20 | <10 | <10 | — | 56 |
| E45 +44 +73 | GAATTATTTCTTCCCCAGTTGCATTCAATG | 30 | <10 | <10 | — | 57 |
| E45 +69 +98 | CTGGCATCTGTTTTTGAGGATTGCTGAATT | 30 | <10 | <10 | — | 58 |
| E45 +34 +59 | CCAGTTGCATTCAATGTTCTGACAAC | 26 | <10 | <10 | — | 59 |
| E45 +56 +78 | TTGCTGAATTATTTCTTCCCCAG | 23 | <10 | <10 | — | 60 |
| E45 +60 +88 | TTTTTGAGGATTG CTGAATTATT TCTTCC | 29 | <10 | <10 | — | 61 |
| E45 +88 +112 | TTTCCTGTAGAATACTGGCA TCTGT | 25 | <10 | <10 | — | 62 |
| E45 +92 +122 | CTTCCCAATTTTTCCTGTAGAATACTGGCAT | 31 | <10 | <10 | — | 63 |
| E45 +94 +118 | CCAATTTTTCCTGTAGAATACTGGC | 25 | <10 | <10 | — | 64 |
| E45 +98 +126 | CAGGCTTCCCAATTTTTCCTGTAGAATAC | 29 | <10 | <10 | — | 65 |

TABLE 2-continued

AO SEQUENCES TARGETING EXON 45

| Antisense oligonucleotide name | Sequences (5' to 3') | Length (bp) | skipping efficiency (%) Human Myoblast | DMD Myoblast | HDMD Mice | SEQ ID No. |
|---|---|---|---|---|---|---|
| E45 +119 +144 | CTCCTGCCACCGCAGATTCAGGCTTC | 26 | <10 | <10 | — | 66 |
| E45 +126 +150 | GCAGACCTCC TGCCACCGCAGATTC | 25 | <10 | <10 | — | 67 |
| E45 +126 +155 | TGTTTGCAGACCTCC TGCCACCGCAGATTC | 30 | <10 | <10 | — | 68 |
| E45 +134 +157 | GCTGTTTGCAGACCTCCTGCCACC | 24 | <10 | <10 | — | 69 |
| E45 +130 +154 | GTTTGCAGACCTCCTGCCACCGCAG | 25 | <10 | <10 | — | 70 |
| E45 +145 +174 | CTTTTTTCTGTCTGACAGCTGTTTGCAGAC | 30 | <10 | <10 | — | 71 |
| E45 +147 +167 | CTGTCTGACAGCTGTTTGCAG | 21 | <10 | <10 | — | 72 |
| E45 +156 -4 | CTACCTCTTTTTTCTGTCTGACAGC | 25 | <10 | <10 | — | 73 |
| E45 +170 -20 | TATTAGATCTGTCGCCCTACCTCTT | 25 | <10 | <10 | — | 74 |
| E45 +174 -22 | CCTATTAGATCTGTCGCCCTACCTC | 25 | <10 | <10 | — | 75 |

In one embodiment, preferred sequences for targeting dystrophin exon 45 include: HE45(-3 +22), HE45(-2 +20), HE45(-8 +21), HE45(-1 +27), HE45(-9 +21), HE45(-3 +27), HE45(-7 +23), HE45(-7 +21), HE45(-5 +23), HE45(-3 +25); SEQ ID NOs 27, 27, 34, 35, 37, 40, 42, 44, 45,46.

Figure 2:
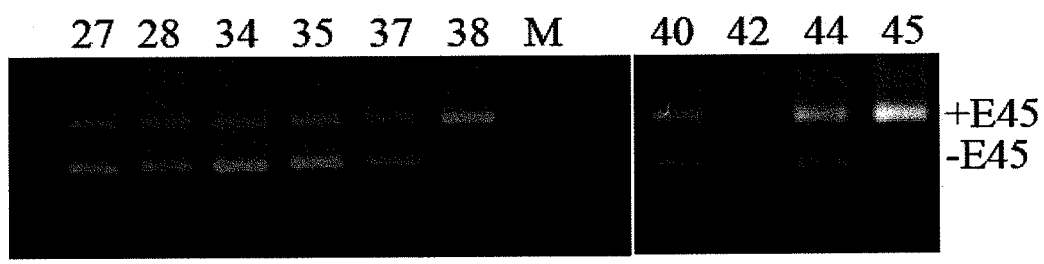

FIG. 2 shows a series of western blots of in vivo exon 45 skipping in the hDMD mice by i.m. injection of 20 μg PMO in conjunction with the use of delivery-enhancing polymer. Exon 45 skipping was detected by RT-PCR. M, size marker. +45, represents transcripts without exon 45 skipping and −45 represents transcripts with exon 45 skipping.

TABLE 3

AO SEQUENCES TARGETING EXON 50

| Antisense oligonucleotide name | Sequences (5' to 3') | Length (bp) | skipping efficiency (%) Human Myoblast | GFP reporter myoblast | HDMD Mice | SEQ ID No. |
|---|---|---|---|---|---|---|
| HE50 (-19 -1) | CUUUAACAGAAAAGCAUAC | 19 | 0 | 0 | — | 76 |
| HE50 (-19 +1) | UCUUUAACAGAAAAGCAUAC | 20 | 0 | 0 | — | 77 |
| HE50(-19 +3) | CCUCUUUAACAGAAAAGCAUAC | 22 | 3 | 4 | — | 78 |
| HE50(-19 +8) | AACUUCCUCUUUAACAGAAAAGCAUAC | 27 | 29 | 21 | 34 | 79 |
| HE50(-19 +13) | CUUCUAACUUCCUCUUUAACAGAAAAGCAUAC | 32 | 1 | 3 | — | 80 |
| HE50(-13 +3) | CCUCUUUAACAGAAAA | 16 | 0 | 0 | — | 81 |
| HE50(-14 +8) | AACUUCCUCUUUAACAGAAAAG | 22 | 0 | 0 | — | 82 |
| HE50(-9 +8) | AACUUCCUCUUUAACAG | 17 | 0 | 0 | — | 83 |
| HE50(-9 +21) | GCUCAGAUCUUCUAACUUCCUCUUUAACAG | 30 | 0 | 0 | — | 84 |
| HE50(-8 +8) | AACUUCCUCUUUAACA | 16 | 0 | 0 | — | 85 |
| HE50(+2 +30) | CCACUCAGAGCUCAGAUCUUCUAACUUCC | 29 | 25 | 8 | 25 | 86 |
| HE50(+11 +27) | CUCAGAGCUCAGAUCUU | 17 | 4 | 2 | — | 87 |
| HE50(+42 +58) | GCUCUUGAAGUAAACGG | 17 | 0 | 0 | 0 | 88 |
| HE50(+85 +102) | AAUAGUGGUCAGUCCAGG | 18 | 0 | 0 | — | 89 |
| HE50(+92 -5) | CUUACAGGCUCCAAUAGUGGUCA | 23 | 0 | 0 | — | 90 |
| HE50(+92 -10) | GUAUACUUACAGGCUCCAAUAGUGGUCA | 28 | 0 | 0 | — | 91 |

TABLE 3-continued

AO SEQUENCES TARGETING EXON 50

| Antisense oligonucleotide name | Sequences (5' to 3') | Length (bp) | skipping efficiency (%) Human Myoblast | GFP reporter myoblast | HDMD Mice | SEQ ID No. |
|---|---|---|---|---|---|---|
| HE50(+94 -14) | UCCAGUAUACUUACAGGCUCCAAUAGUGGU | 30 | 0 | 0 | 0 | 92 |
| HE50(+97 -5) | CUUACAGGCUCCAAUAGU | 18 | 0 | 3 | — | 93 |
| HE50(+97 -10) | GUAUACUUACAGGCUCCAAUAGU | 23 | 0 | 0 | — | 94 |
| HE50(+97 -14) | UCCAGUAUACUUACAGGCUCCAAUAGU | 27 | 0 | 1 | — | 95 |
| HE50(+102 -14) | UCCAGUAUACUUACAGGCUCCA | 22 | 1 | 3 | — | 96 |
| HE50(+103 -18) | GGGAUCCAGUAUACUUACAGGCUCC | 25 | 65 | 28 | 62 | 97 |
| HE50(+105 -14) | UCCAGUAUACUUACAGGCU | 19 | 0 | 6 | — | 98 |
| HE50(+109 -14) | UCCAGUAUACUUACA | 15 | 0 | 0 | — | 99 |

In one embodiment, preferred AO sequences for targeting dystrophin exon 50: HE50(-19 +8) (79), HE50(+103 -18) (SEQ ID NO 97).

Figure 3:
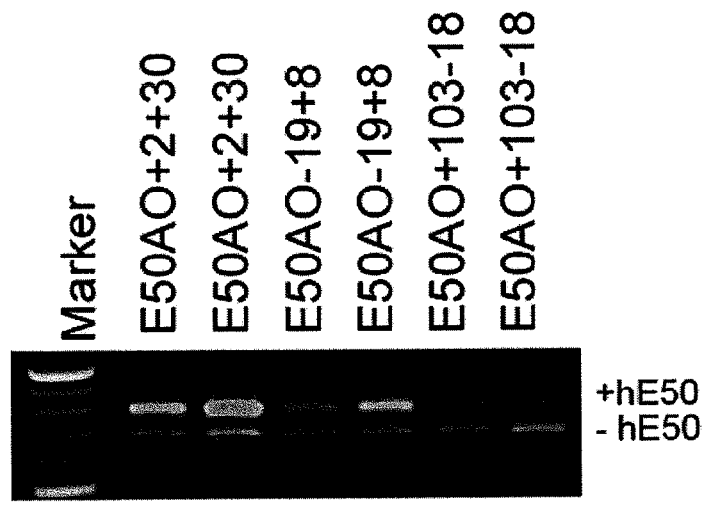

FIG. 3 is an in vivo demonstration of PMOs targeting human dystrophin exon 50 in the hDMD mice by local i.m. injection of 20 µg PMO in conjunction with the use of delivery-enhancing polymer. Duplicate for each PMO. Top bands represent the transcripts without human dystrophin exon 50 skipping (+hE50); bottom bands represent the transcripts with human dystrophin exon 50 skipping (-hE50). The correct skipping of exon 50 was confirmed by sequencing of the bands.

Figure 4:
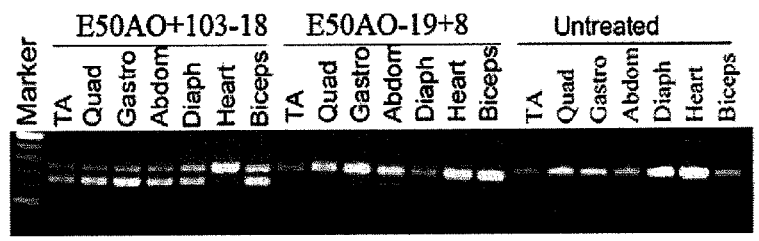

FIG. 4 shows the effect of PMO (tagged with vivo-polymer by Genetools) for human dystrophin exon 50 skipping systemically in the hDMD mice. TA, tibialis anterior; Quad, quadriceps; Gastro, gastronemium; Abdom, abdominal; Diaph, diaphragm. The signal intensity of the bands representing human dystrophin exon 50 skipping was up to 80% and 15% in the muscles treated with Vivo-hE50AO+103-18 and Vivo-hE50AO-19+8 respectively (measured with NIH ImagJ).

TABLE 4

AO SEQUENCES TARGETING EXON 51

| Antisense oligonucleotide name | Sequences (5' to 3') | Length (bp) | skipping efficiency (%) Human Myoblast | DMD Myoblast | HDMD Mice | SEQ ID No. |
|---|---|---|---|---|---|---|
| HE51 (+68 +95) | CTCCAACATCAAGGAAGATGGCATTTCT | 28 | 50 | — | 35 | 100 |
| HE51 (+65 +89) | CATCAAGGAAGATGGCATTTCTAGT | 25 | 40 | — | 18 | 101 |
| HE51 (-22 +4) | GGAGCTAAAATAMTGGGTTMGC | 26 | 2 | — | 5 | 102 |
| HE51 (+220 -11) | TTTTCTCATACCTTCTGCTTGATGA | 25 | 0 | — | — | 103 |
| HE51 (+74 +101) | AGGTACCTCCAACATCAAGGAAGATGG | 28 | 5 | — | — | 104 |
| HE51(+71 +95) | CTCCAACATCAAGGAAGATGGCATT | 25 | 15 | — | <5 | 105 |
| HE51(+68 +95) | CTCCAACATCAAGGAAGATGGCATTTCT | 28 | 5 | — | — | 106 |
| HE51 (+66 +95) | CTCCAACATCAAGGAAGATGGCATTTCTAG | 30 | 0 | — | — | 107 |
| HE51 (+61 +85) | AAGGAAGATGGCATTTCTAGTTTGG | 25 | 20 | — | <5 | 108 |
| HE51(-10 +15) | CAGTCTGAGTAGGAGCTAAAATATT | 25 | 0 | — | — | 109 |
| HE51(-16 +9) | GAGTAGGAGCTAAAATATTTTGGGT | 25 | 0 | — | — | 110 |

In one embodiment, preferred AO sequences for targeting dystrophin exon 51 include: HE51 (+68 +95), (100) HE51 (+65 +89) (SEQ ID NO 101).

FIG. 5 is a western blot showing in vivo exon 51 skipping in the hDMD mice by i.m. injection of 20 µg PMO in conjunction with the use of delivery-enhancing polymer. Exon 51 skipping was detected by RT-PCR. M, size marker. +51, represents transcripts without exon 51 skipping and −51 represents transcripts with exon 51 skipping.

TABLE 5

AO SEQUENCES TARGETING EXON 53

| Antisense oligonucleotide name | Sequences (5' to 3') | Length (bp) | skipping efficiency (%) Human Myoblast | DMD Myoblast | HDMD Mice | SEQ ID No. |
|---|---|---|---|---|---|---|
| HE53 (−11 +14) | CUGAAUUCUUUCAACUAGAAUAAAA | 25 | 0 | — | — | 111 |
| HE53 (+69 +96) | GCCAUUGUGUUGAAUCCUUUAACAUUUC | 28 | 0 | — | — | 112 |
| HE53 (+134 +158) | CCAUGACUCAAGCUUGGCUCUGGCC | 25 | 0 | — | — | 113 |
| HE53 (+168 +187) | CCCUAUACAGUAGAUGCAAU | 20 | 0 | — | — | 114 |
| HE53 (+200 −11) | UUGAUACUAACCUUGGUUUCUGUG | 24 | 0 | — | — | 115 |
| HE53 (+42 +65) | CAACTGTTGCCTCCGGTTCTGAAG | 24 | 20 | — | 10 | 116 |
| HE53 (+146 +169) | GGACCCTCCTTCCATGACTCAAGC | 24 | 0 | — | 0 | 117 |
| HE53 (+204 −18) | GGTATCTTTGATACTAACCTTGGTTTC | 27 | 15 | — | 6 | 118 |

In one embodiment, preferred AO sequences for targeting dystrophin exon 53 include: HE53 (+42 +65) (SEQ ID NO 116).

FIG. 6 is a western blot showing in vivo exon 53 skipping in the hDMD mice by i.m. injection of 20 uµ PMO in conjunction with the use of delivery-enhancing polymer. Exon 53 skipping was detected by RT-PCR. M, size marker. +53, represents transcripts without exon 53 skipping and −53 represents transcripts with exon 53 skipping.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An antisense oligonucleotide molecule for treating DMD, the antisense oligonucleotide molecule consisting of a base sequence of

CCAATGCCATCCTGGAGTTCCT (SEQ ID NO: 28)

and analogs and combinations thereof,
  wherein the analogs have a base sequence that varies from any one of the foregoing base sequences by:
    1) substitution of one or more T bases with U bases, or vice versa;
    2) deletion or substitution of up to two bases;
    3) addition of one base to one or both ends of the sequence; or
    4) deletion of one base at one or more ends of the sequence; and
  wherein the molecule can bind to a target site to cause exon skipping in an exon of the dystrophin gene.

2. The antisense oligonucleotide molecule according to claim 1, wherein the exon of the dystrophin gene at which exon skipping is caused is exon 45.

3. The antisense oligonucleotide molecule according to claim 1, wherein the antisense oligonucleotide molecule is conjugated to or complexed with a distinct chemical entity.

4. The antisense oligonucleotide molecule according to claim 1, wherein the antisense oligonucleotide molecule is a phosphorodiamidate morpholino oligonucleotide (PMO).

5. The antisense oligonucleotide molecule according to claim 1, wherein the antisense oligonucleotide molecule is an oligomer which is capable of binding to its complementary RNA sequence.

6. The antisense oligonucleotide molecule according to claim 1, wherein the antisense oligonucleotide molecule includes a deletion of one to two nucleotide bases at either end thereof.

7. A pharmaceutical composition for treating DMD, the composition comprising an antisense oligonucleotide molecule according to claim 1, and a pharmaceutically acceptable carrier, adjuvant or vehicle.

8. A pharmaceutical composition comprising an antisense oligonucleotide conjugated with a polymer to enhance the delivery of antisense oligonucleotide and antisense effect, wherein the antisense oligonucleotide is

CCAATGCCATCCTGGAGTTCCT (SEQ ID NO: 28)

and analogs and combinations thereof,
  wherein the analogs have a base sequence that varies from any one of the foregoing base sequences by:
    1) substitution of one or more T bases with U bases, or vice versa;

2) deletion or substitution of up to two bases;
3) addition of one base to one or both ends of the sequence; or
4) deletion of one base at one or more ends of the sequence; and wherein the molecule can bind to a target site to cause exon skipping in an exon of the dystrophin gene.

9. The composition of claim 8, wherein the antisense oligonucleotide is a morpholino oligomer or a PNA oligomer.

10. The composition of claim 8, wherein the antisense oligonucleotide comprises a phosphorodiamidate-linked morpholino oligomer.

11. The composition of claim 8, wherein the polymer is a peptide.

* * * * *